(12) United States Patent
Brady et al.

(10) Patent No.: US 7,713,299 B2
(45) Date of Patent: May 11, 2010

(54) HAPTIC FOR ACCOMMODATING INTRAOCULAR LENS

(75) Inventors: Daniel G. Brady, San Juan Capistrano, CA (US); Tuyet Hoc Nguyen, Orange, CA (US); Henk A. Weeber, Groningen (NL); Douglas S. Cali, Mission Viejo, CA (US)

(73) Assignee: Abbott Medical Optics Inc., Santa Ana, CA (US)

( * ) Notice: Subject to any disclaimer, the term of this patent is extended or adjusted under 35 U.S.C. 154(b) by 33 days.

(21) Appl. No.: 11/618,325

(22) Filed: Dec. 29, 2006

(65) Prior Publication Data

US 2008/0161913 A1 Jul. 3, 2008

(51) Int. Cl.
*A61F 2/16* (2006.01)

(52) U.S. Cl. .................. 623/6.46; 623/6.47; 623/6.49

(58) Field of Classification Search ........ 623/6.37–6.49
See application file for complete search history.

(56) References Cited

U.S. PATENT DOCUMENTS

| | | |
|---|---|---|
| 1,483,509 A | 2/1924 | Bugbee |
| 2,129,305 A | 9/1938 | Feinbloom |
| 2,274,142 A | 2/1942 | Houchin |
| 2,405,989 A | 6/1946 | Beach |
| 2,511,517 A | 6/1950 | Spiegel |
| 2,834,023 A | 5/1958 | Lieb |
| 3,004,470 A | 10/1961 | Ruhle |
| 3,031,927 A | 5/1962 | Wesley |
| 3,034,403 A | 5/1962 | Neefe |
| RE25,286 E | 11/1962 | DeCarle |
| 3,210,894 A | 10/1965 | Bentley et al. |
| 3,227,507 A | 1/1966 | Feinbloom |
| 3,339,997 A | 9/1967 | Wesley |
| 3,420,006 A | 1/1969 | Barnett |
| 3,431,327 A | 3/1969 | Tsuetaki |
| 3,482,906 A | 12/1969 | Volk |
| 3,542,461 A | 11/1970 | Girard et al. |
| 3,673,616 A | 7/1972 | Fedorov et al. |
| 3,693,301 A | 9/1972 | Lemaltre |

(Continued)

FOREIGN PATENT DOCUMENTS

AU   3225789   10/1989

(Continued)

OTHER PUBLICATIONS

U.S. Appl. No. 10/280,918 filed Aug. 5, 2003.

(Continued)

*Primary Examiner*—Suzette J Gherbi

(57) ABSTRACT

An intraocular lens is disclosed, with an optic that changes shape in response to a deforming force exerted by the zonules of the eye. A haptic supports the optic around its equator and couples the optic to the capsular bag of the eye. The region of contact between the optic and the haptic extends into the edge of the optic, similar to the interface between a bicycle tire and the rim that holds it in place. The haptic may be stiffer than the optic. The haptic may have the same refractive index as the optic. The haptic may include a saddle-shaped portion in contact with the adjustable optic, with a convex profile along an optical axis; and a concave profile in a plane perpendicular to the optical axis.

26 Claims, 21 Drawing Sheets

U.S. PATENT DOCUMENTS

| | | |
|---|---|---|
| 3,711,870 A | 1/1973 | Deltrick |
| 3,718,870 A | 2/1973 | Keller |
| 3,794,414 A | 2/1974 | Wesley |
| 3,866,249 A | 2/1975 | Fiom |
| 3,906,551 A | 9/1975 | Otter |
| 3,913,148 A | 10/1975 | Potthast |
| 3,922,728 A | 12/1975 | Krasnov |
| 3,925,825 A | 12/1975 | Richards et al. |
| 3,932,148 A | 1/1976 | Krewalk, Sr. |
| 4,010,496 A | 3/1977 | Neefe |
| 4,014,049 A | 3/1977 | Richards et al. |
| 4,041,552 A | 8/1977 | Ganias |
| 4,053,953 A | 10/1977 | Flom et al. |
| 4,055,378 A | 10/1977 | Feneberg et al. |
| 4,056,855 A | 11/1977 | Kelman |
| 4,062,629 A | 12/1977 | Winthrop |
| 4,073,579 A | 2/1978 | Deeg et al. |
| 4,074,368 A | 2/1978 | Levy, Jr. et al. |
| 4,087,866 A | 5/1978 | Choyce et al. |
| 4,110,848 A | 9/1978 | Jensen |
| 4,159,546 A | 7/1979 | Shearing |
| 4,162,122 A | 7/1979 | Cohen |
| 4,195,919 A | 4/1980 | Shelton |
| 4,199,231 A | 4/1980 | Evans |
| 4,210,391 A | 7/1980 | Cohen |
| 4,240,719 A | 12/1980 | Guilino et al. |
| 4,244,060 A | 1/1981 | Hoffer |
| 4,244,597 A | 1/1981 | Dandl |
| 4,251,887 A | 2/1981 | Anis |
| 4,253,199 A | 3/1981 | Banko |
| 4,254,509 A | 3/1981 | Tennant |
| 4,261,065 A | 4/1981 | Tennant |
| 4,274,717 A | 6/1981 | Davenport |
| 4,285,072 A | 8/1981 | Morcher et al. |
| 4,298,994 A | 11/1981 | Clayman |
| 4,307,945 A | 12/1981 | Kitchen et al. |
| 4,315,336 A | 2/1982 | Poler |
| 4,315,673 A | 2/1982 | Guilino et al. |
| 4,316,293 A | 2/1982 | Bayers |
| 4,338,005 A | 7/1982 | Cohen |
| 4,340,283 A | 7/1982 | Cohen |
| 4,340,979 A | 7/1982 | Kelman |
| 4,361,913 A | 12/1982 | Streck |
| 4,370,760 A | 2/1983 | Kelman |
| 4,373,218 A | 2/1983 | Schachar |
| 4,377,329 A | 3/1983 | Poler |
| 4,377,873 A | 3/1983 | Reichert, Jr. |
| 4,402,579 A | 9/1983 | Poler |
| 4,404,694 A | 9/1983 | Kelman |
| 4,409,691 A | 10/1983 | Levy |
| 4,418,991 A | 12/1983 | Breger |
| 4,424,597 A | 1/1984 | Schlegel |
| 4,442,553 A | 4/1984 | Hessburg |
| 4,463,458 A | 8/1984 | Seidner |
| 4,476,591 A | 10/1984 | Arnott |
| 4,504,981 A | 3/1985 | Walman |
| 4,504,982 A | 3/1985 | Burk |
| 4,512,040 A | 4/1985 | McClure |
| 4,551,864 A | 11/1985 | Akhavi |
| 4,560,383 A | 12/1985 | Leiske |
| 4,562,600 A | 1/1986 | Ginsberg et al. |
| 4,573,775 A | 3/1986 | Bayshore |
| 4,573,998 A | 3/1986 | Mazzocco |
| 4,575,878 A | 3/1986 | Dubroff |
| 4,580,882 A | 4/1986 | Nuchman et al. |
| 4,581,033 A | 4/1986 | Callahan |
| 4,596,578 A | 6/1986 | Kelman |
| 4,615,701 A | 10/1986 | Woods |
| 4,617,023 A | 10/1986 | Peyman |
| 4,618,228 A | 10/1986 | Baron et al. |
| 4,618,229 A | 10/1986 | Jacobstein et al. |
| 4,629,460 A | 12/1986 | Dyer |
| 4,636,049 A | 1/1987 | Blaker |
| 4,636,211 A | 1/1987 | Nielsen et al. |
| 4,637,697 A | 1/1987 | Freeman |
| 4,641,934 A | 2/1987 | Freeman |
| 4,661,108 A | 4/1987 | Grendahl et al. |
| 4,664,666 A | 5/1987 | Barrett |
| 4,676,792 A | 6/1987 | Praeger |
| 4,687,484 A | 8/1987 | Kaplan |
| 4,693,572 A | 9/1987 | Tsuetaki et al. |
| 4,693,716 A | 9/1987 | Mackool |
| RE32,525 E | 10/1987 | Pannu |
| 4,702,244 A | 10/1987 | Mazzocco |
| 4,704,016 A | 11/1987 | DeCarle |
| 4,710,194 A | 12/1987 | Kelman |
| 4,720,286 A | 1/1988 | Bailey et al. |
| 4,725,278 A | 2/1988 | Shearing |
| 4,731,078 A | 3/1988 | Stoy et al. |
| 4,737,322 A | 4/1988 | Bruns et al. |
| 4,752,123 A | 6/1988 | Blaker |
| 4,759,762 A | 7/1988 | Grendahl |
| 4,769,033 A | 9/1988 | Nordan |
| 4,769,035 A | 9/1988 | Kelman |
| 4,787,903 A | 11/1988 | Grendahl |
| 4,790,847 A | 12/1988 | Woods |
| 4,813,955 A | 3/1989 | Achatz et al. |
| 4,816,032 A | 3/1989 | Hetland |
| 4,830,481 A | 5/1989 | Futhey et al. |
| 4,840,627 A | 6/1989 | Blumenthal |
| 4,842,601 A | 6/1989 | Smith |
| 4,878,910 A | 11/1989 | Koziol et al. |
| 4,878,911 A | 11/1989 | Anis |
| 4,881,804 A | 11/1989 | Cohen |
| 4,888,012 A | 12/1989 | Horn et al. |
| 4,888,015 A | 12/1989 | Domino |
| 4,888,016 A | 12/1989 | Langerman |
| 4,890,912 A | 1/1990 | Visser |
| 4,890,913 A | 1/1990 | DeCarle |
| 4,892,543 A | 1/1990 | Turley |
| 4,898,461 A | 2/1990 | Portney |
| 4,906,246 A | 3/1990 | Grendahl |
| 4,917,681 A | 4/1990 | Nordan |
| 4,919,663 A | 4/1990 | Grendahl |
| 4,921,496 A | 5/1990 | Grendahl |
| 4,923,296 A | 5/1990 | Erickson |
| 4,932,966 A | 6/1990 | Christie et al. |
| 4,932,968 A | 6/1990 | Caldwell et al. |
| 4,938,583 A | 7/1990 | Miller |
| 4,946,469 A | 8/1990 | Sarfarazi |
| 4,955,902 A | 9/1990 | Kelman |
| 4,976,534 A | 12/1990 | Milge et al. |
| 4,976,732 A | 12/1990 | Vorosmarthy |
| 4,990,159 A | 2/1991 | Kraff |
| 4,994,058 A | 2/1991 | Raven et al. |
| 4,994,082 A | 2/1991 | Richards et al. |
| 4,994,083 A | 2/1991 | Sulc et al. |
| 5,000,559 A | 3/1991 | Takahashi et al. |
| 5,002,382 A | 3/1991 | Seidner |
| 5,019,098 A | 5/1991 | Mercier |
| 5,019,099 A | 5/1991 | Nordan |
| 5,047,051 A | 9/1991 | Cumming |
| 5,047,052 A | 9/1991 | Dubroff |
| 5,071,432 A | 12/1991 | Baikoff |
| 5,089,024 A | 2/1992 | Christie et al. |
| 5,096,285 A | 3/1992 | Silberman |
| 5,112,351 A | 5/1992 | Christie et al. |
| 5,129,718 A | 7/1992 | Futhey et al. |
| 5,147,397 A | 9/1992 | Christ et al. |
| 5,152,789 A | 10/1992 | Willis |
| 5,158,572 A | 10/1992 | Nielsen |
| 5,166,711 A | 11/1992 | Portney |
| 5,166,712 A | 11/1992 | Portney |
| 5,171,266 A | 12/1992 | Wilkey et al. |

| | | |
|---|---|---|
| 5,173,723 A | 12/1992 | Volk |
| 5,192,317 A | 3/1993 | Kalb |
| 5,192,318 A | 3/1993 | Schneider |
| 5,201,762 A | 4/1993 | Hauber |
| 5,225,858 A | 7/1993 | Portney |
| 5,258,025 A | 11/1993 | Fedorov et al. |
| 5,260,727 A | 11/1993 | Oksman et al. |
| 5,270,744 A | 12/1993 | Portney |
| 5,275,623 A | 1/1994 | Sarfarazi |
| 5,354,335 A | 10/1994 | Lipshitz et al. |
| RE34,988 E | 7/1995 | Langerman |
| 5,443,506 A | 8/1995 | Garabet |
| 5,476,514 A | 12/1995 | Cumming |
| 5,480,428 A | 1/1996 | Fedorov et al. |
| 5,489,302 A * | 2/1996 | Skottun ................ 623/6.13 |
| 5,496,366 A | 3/1996 | Cumming |
| 5,521,656 A | 5/1996 | Portney |
| 5,562,731 A | 10/1996 | Cumming |
| 5,574,518 A | 11/1996 | Mercure |
| 5,578,081 A | 11/1996 | McDonald |
| 5,593,436 A | 1/1997 | Langerman |
| 5,607,472 A | 3/1997 | Thompson |
| 5,628,795 A | 5/1997 | Langerman |
| 5,628,796 A | 5/1997 | Suzuki |
| 5,628,797 A | 5/1997 | Richer |
| 5,652,014 A | 7/1997 | Galin et al. |
| 5,652,638 A | 7/1997 | Roffman et al. |
| 5,657,108 A | 8/1997 | Portney |
| 5,674,282 A | 10/1997 | Cumming |
| 5,682,223 A | 10/1997 | Menezes et al. |
| 5,684,560 A | 11/1997 | Roffman et al. |
| 5,766,244 A | 6/1998 | Binder |
| 5,769,890 A | 6/1998 | McDonald |
| 5,776,191 A | 7/1998 | Mazzocco |
| 5,776,192 A | 7/1998 | McDonald |
| 5,814,103 A | 9/1998 | Lipshitz et al. |
| 5,824,074 A | 10/1998 | Koch |
| 5,843,188 A | 12/1998 | McDonald |
| 5,847,802 A | 12/1998 | Menezes et al. |
| 5,876,442 A | 3/1999 | Lipshitz et al. |
| 5,898,473 A | 4/1999 | Seidner et al. |
| 5,968,094 A | 10/1999 | Werblin et al. |
| 6,013,101 A | 1/2000 | Israel |
| 6,051,024 A | 4/2000 | Cumming |
| 6,083,261 A * | 7/2000 | Callahan et al. .......... 623/6.38 |
| 6,096,078 A | 8/2000 | McDonald |
| 6,110,202 A | 8/2000 | Barraquer et al. |
| 6,117,171 A | 9/2000 | Skottun |
| 6,136,026 A | 10/2000 | Israel |
| 6,152,958 A | 11/2000 | Nordan |
| 6,176,878 B1 | 1/2001 | Gwon et al. |
| 6,197,058 B1 | 3/2001 | Portney |
| 6,200,342 B1 | 3/2001 | Tassignon |
| 6,217,612 B1 | 4/2001 | Woods |
| 6,231,603 B1 | 5/2001 | Lang et al. |
| 6,299,641 B1 | 10/2001 | Woods |
| 6,302,911 B1 | 10/2001 | Hanna |
| 6,322,589 B1 | 11/2001 | Cumming |
| 6,399,734 B1 * | 6/2002 | Hodd et al. .................. 528/32 |
| 6,406,494 B1 | 6/2002 | Laguette et al. |
| 6,443,985 B1 | 9/2002 | Woods |
| 6,485,516 B2 | 11/2002 | Boehm |
| 6,488,708 B2 | 12/2002 | Sarfarazi |
| 6,503,276 B2 | 1/2003 | Lang et al. |
| 6,524,340 B2 | 2/2003 | Israel |
| 6,551,354 B1 | 4/2003 | Ghazizadeh et al. |
| 6,554,859 B1 | 4/2003 | Lang et al. |
| 6,558,420 B2 | 5/2003 | Green |
| 6,592,621 B1 | 7/2003 | Domino |
| 6,599,317 B1 | 7/2003 | Weinschenk, III et al. |
| 6,616,691 B1 | 9/2003 | Tran |
| 6,616,692 B1 | 9/2003 | Glick et al. |
| 6,638,305 B2 | 10/2003 | Laguette |
| 6,638,306 B2 | 10/2003 | Cumming |
| 6,645,246 B1 | 11/2003 | Weinschenk, III et al. |
| 6,660,035 B1 | 12/2003 | Lang et al. |
| 6,749,633 B1 | 6/2004 | Lorenzo et al. |
| 6,749,634 B2 | 6/2004 | Hanna |
| 6,855,164 B2 | 2/2005 | Glazier |
| 7,018,409 B2 | 3/2006 | Glick et al. |
| 7,025,783 B2 | 4/2006 | Brady et al. |
| 7,097,660 B2 | 8/2006 | Portney |
| 7,125,422 B2 | 10/2006 | Woods et al. |
| 7,150,759 B2 | 12/2006 | Paul et al. |
| 7,220,279 B2 | 5/2007 | Nun |
| 7,223,288 B2 * | 5/2007 | Zhang et al. ............... 623/6.34 |
| 7,503,938 B2 | 3/2009 | Phillips |
| 2002/0111678 A1 | 8/2002 | Zadno-Azizi et al. |
| 2002/0116058 A1 | 8/2002 | Zadno-Azizi et al. |
| 2002/0120329 A1 | 8/2002 | Lang et al. |
| 2002/0188351 A1 | 12/2002 | Laguette |
| 2003/0060878 A1 | 3/2003 | Shadduck |
| 2003/0060881 A1 | 3/2003 | Glick et al. |
| 2003/0109926 A1 | 6/2003 | Portney |
| 2003/0130732 A1 | 7/2003 | Sarfarazi |
| 2003/0135272 A1 | 7/2003 | Rady et al. |
| 2003/0149480 A1 | 8/2003 | Shadduck |
| 2003/0187505 A1 | 10/2003 | Liao |
| 2003/0204254 A1 | 10/2003 | Peng et al. |
| 2003/0204255 A1 | 10/2003 | Peng et al. |
| 2004/0054408 A1 | 3/2004 | Glick et al. |
| 2004/0082993 A1 | 4/2004 | Woods |
| 2004/0082994 A1 | 4/2004 | Woods et al. |
| 2004/0111153 A1 * | 6/2004 | Woods et al. ............... 623/6.37 |
| 2004/0158322 A1 | 8/2004 | Shen |
| 2004/0167621 A1 | 8/2004 | Peyman |
| 2004/0181279 A1 | 9/2004 | Nun |
| 2004/0215340 A1 | 10/2004 | Messner et al. |
| 2005/0021139 A1 * | 1/2005 | Shadduck ................... 623/6.35 |
| 2005/0027354 A1 * | 2/2005 | Brady et al. ............... 623/6.31 |
| 2005/0085906 A1 | 4/2005 | Hanna |
| 2005/0085907 A1 | 4/2005 | Hanna |
| 2005/0125057 A1 * | 6/2005 | Cumming ................... 623/6.37 |
| 2005/0131535 A1 | 6/2005 | Woods |
| 2005/0137703 A1 | 6/2005 | Chen |
| 2005/0288785 A1 * | 12/2005 | Portney et al. ............. 623/6.46 |
| 2006/0064162 A1 | 3/2006 | Klima |
| 2006/0111776 A1 | 5/2006 | Glick et al. |
| 2006/0116765 A1 * | 6/2006 | Blake et al. ................ 623/6.46 |
| 2007/0078515 A1 * | 4/2007 | Brady ....................... 623/6.37 |
| 2007/0106381 A1 * | 5/2007 | Blake ........................ 623/6.37 |
| 2007/0123591 A1 | 6/2007 | Klima |
| 2007/0129798 A1 | 6/2007 | Chawdhary |
| 2007/0135915 A1 | 6/2007 | Klima |
| 2007/0299487 A1 * | 12/2007 | Shadduck ..................... 607/89 |
| 2008/0161913 A1 | 7/2008 | Brady |
| 2008/0161914 A1 | 7/2008 | Brady et al. |
| 2009/0012609 A1 | 1/2009 | Geraghty et al. |

FOREIGN PATENT DOCUMENTS

| | | |
|---|---|---|
| CH | 681687 | 5/1993 |
| CH | 681687 A5 | 5/1993 |
| DE | 2702117 | 7/1978 |
| DE | 3246306 | 6/1984 |
| DE | 4038088 | 6/1992 |
| DE | 19501444 | 7/1996 |
| EP | 0064812 | 11/1982 |
| EP | 0246216 | 11/1987 |
| EP | 0328117 | 8/1989 |
| EP | 0329981 | 8/1989 |
| EP | 0337390 | 10/1989 |
| EP | 0342895 | 11/1989 |
| EP | 0351471 | 1/1990 |
| EP | 0356050 | 2/1990 |
| EP | 0488835 | 6/1992 |

| | | |
|---|---|---|
| EP | 0507292 | 10/1992 |
| EP | 0566170 | 10/1993 |
| EP | 0601845 | 6/1994 |
| EP | 0691109 | 1/1996 |
| EP | 0897702 | 2/1999 |
| EP | 0766540 | 4/1999 |
| EP | 766540 B1 | 8/1999 |
| GB | 2058391 | 4/1981 |
| GB | 2124500 | 2/1984 |
| GB | 2129155 | 5/1984 |
| GB | 2146791 | 4/1985 |
| GB | 2192291 | 1/1988 |
| GB | 2215076 | 9/1989 |
| WO | 86/03961 | 7/1986 |
| WO | 87/00299 | 1/1987 |
| WO | 87/07496 | 12/1987 |
| WO | 89/02251 | 3/1989 |
| WO | 89/11672 | 11/1989 |
| WO | 90/00889 | 2/1990 |
| WO | 93/05733 | 4/1993 |
| WO | 94/16648 | 8/1994 |
| WO | 95/03783 | 2/1995 |
| WO | 96/10968 | 4/1996 |
| WO | 96/15734 | 5/1996 |
| WO | 96/25126 | 8/1996 |
| WO | 97/12272 | 4/1997 |
| WO | 97/27825 | 8/1997 |
| WO | 97/43984 | 11/1997 |
| WO | 98/56315 | 12/1998 |
| WO | 00/61036 | 4/2000 |
| WO | 00/27315 | 5/2000 |
| WO | 00/66039 | 11/2000 |
| WO | 01/19288 | 3/2001 |
| WO | 01/34066 | 5/2001 |
| WO | 01/34067 | 5/2001 |
| WO | 02/19949 | 3/2002 |
| WO | 03/015669 | 2/2003 |
| WO | 03/034949 A2 | 5/2003 |
| WO | 03/059208 | 7/2003 |
| WO | 03/075810 A1 | 9/2003 |
| WO | 2005/018504 | 3/2005 |
| WO | 2007/040964 | 4/2007 |
| WO | 2007/067872 | 6/2007 |
| WO | 2007-067872 | 6/2007 |
| WO | 2007/067872 A2 | 6/2007 |
| ZA | 888414 | 10/1988 |

OTHER PUBLICATIONS

U.S. Appl. No. 10/280,937 filed Oct. 25, 2005.
Fechner et al. *Iris-claw lens in phakic eyes to correct hyperopia: preliminary study. J. Cataract Refract. Surg.*, Jan. 24, 1998.
Mandell, *Contact Lens Practice*, 4$^{th}$ Ed.
Menezo et al. *Endothelial study of iris-claw phakic lens: four year follow-up. J. Cataract Refract. Surg.*, Aug. 24, 1998.
Thornton, *Accommodation in Pseudophakia*, 25, p. 159.
AMO Specs, Model AC-21 B, 1992.
Study Design of Nuvita, Mar. 20, 1997.
Program from ASCRS Symposium showing video tape between Apr. 10-14, 1999.
DVD titled "New elliptical accommodative IOL for cataract surgery" shown at ASCRS Symposium on Apr. 10, 1999.
U.S. Appl. No. 11/618,411—Pending claims submitted on Jul. 29, 2009.
U.S. Appl. No. 11/966,365—Pending claims submitted on Dec. 28, 2007.

* cited by examiner

HAPTIC FOR ACCOMMODATING INTRAOCULAR LENS

BACKGROUND OF THE INVENTION

1. Field of the Invention

The present invention is directed to intraocular lenses, and more particularly to accommodating intraocular lenses.

2. Description of the Related Art

A human eye can suffer diseases that impair a patients vision. For instance, a cataract may increase the opacity of the lens, causing blindness. To restore the patients vision, the diseased lens may be surgically removed and replaced with an artificial lens, known as an intraocular lens, or IOL. An IOL may also be used for presbyopic lens exchange.

The simplest IOLs have a single focal length, or, equivalently, a single power. Unlike the eye's natural lens, which can adjust its focal length within a particular range in a process known as accommodation, these single focal length IOLs cannot generally accommodate. As a result, objects at a particular position away from the eye appear in focus, while objects at an increasing distance away from that position appear increasingly blurred.

An improvement over the single focal length IOLs is an accommodating IOL, which can adjust its power within a particular range. As a result, the patient can clearly focus on objects in a range of distances away from the eye, rather than at a single distance. This ability to accommodate is of tremendous benefit for the patient, and more closely approximates the patient's natural vision than a single focal length IOL.

When the eye focuses on a relatively distant object, the lens power is at the low end of the accommodation range, which may be referred to as the "far" power. When the eye focuses on a relatively close object, the lens power is at the high end of the accommodation range, which may be referred to as the "near" power. The accommodation range or add power is defined as the near power minus the far power. In general, an accommodation range of 2 to 4 diopters is considered sufficient for most patients.

The human eye contains a structure known as the capsular bag, which surrounds the natural lens. The capsular bag is transparent, and serves to hold the lens. In the natural eye, accommodation is initiated by the ciliary muscle and a series of zonular fibers, also known as zonules. The zonules are located in a relatively thick band mostly around the equator of the lens, and impart a largely radial force to the capsular bag that can alter the shape and/or the location of the natural lens and thereby change its effective power.

In a typical surgery in which the natural lens is removed from the eye, the lens material is typically broken up and vacuumed out of the eye, but the capsular bag is left intact. The remaining capsular bag is extremely useful for an accommodating intraocular lens, in that the eye's natural accommodation is initiated at least in part by the zonules through the capsular bag. The capsular bag may be used to house an accommodating IOL, which in turn can change shape and/or shift in some manner to affect the power and/or the axial location of the image.

The IOL has an optic, which refracts light that passes through it and forms an image on the retina, and a haptic, which mechanically couples the optic to the capsular bag. During accommodation, the zonules exert a force on the capsular bag, which in turn exerts a force on the optic. The force may be transmitted from the capsular bag directly to the optic, or from the capsular bag through the haptic to the optic.

A desirable optic for an accommodating IOL is one that distorts in response to a squeezing or expanding radial force applied largely to the equator of the optic (i.e., by pushing or pulling on or near the edge of the optic, circumferentially around the optic axis). Under the influence of a squeezing force, the optic bulges slightly in the axial direction, producing more steeply curved anterior and/or posterior faces, and producing an increase in the power of the optic. Likewise, an expanding radial force produces a decrease in the optic power by flattening the optic. This change in power is accomplished in a manner similar to that of the natural eye and is well adapted to accommodation. Furthermore, this method of changing the lens power reduces any undesirable pressures exerted on some of the structures in the eye.

One challenge in implementing such an optic is designing a suitable haptic to couple the optic to the capsular bag. The haptic should allow distortion of the optic in an efficient manner, so that a relatively small ocular force from the ciliary muscle, zonules, and/or capsular bag can produce a relatively large change in power and/or axial location of the image. This reduces fatigue on the eye, which is highly desirable.

Accordingly, there exists a need for an intraocular lens having a haptic with increased efficiency in converting an ocular force to a change in power and/or a change in axial location of the image.

SUMMARY OF THE INVENTION

An embodiment is an intraocular lens for implantation in a capsular bag of an eye, comprising an adjustable optic; and a haptic protruding into the adjustable optic. The haptic is configured to transmit forces to alter at least one of the shape or the thickness of the adjustable optic.

A further embodiment is an intraocular lens for implantation in a capsular bag of an eye, comprising an adjustable optic having an optic stiffness and an optic refractive index; and a haptic having a haptic stiffness and a haptic refractive index for coupling the adjustable optic to the capsular bag. The haptic stiffness is greater than the optic stiffness. The haptic refractive index is essentially equal to the optic refractive index.

A further embodiment is a method of adjusting the focus of an intraocular lens having an adjustable optic having an annular recess, comprising applying a deforming force through a haptic in contact with the annular recess of the adjustable optic; and altering at least one parameter of the adjustable optic in response to the deforming force.

DETAILED DESCRIPTION OF THE DRAWINGS

In a healthy human eye, the natural lens is housed in a structure known as the capsular bag. The capsular bag is driven by a ciliary muscle and zonular fibers (also known as zonules) in the eye, which can compress and/or pull on the capsular bag to change its shape. The motions of the capsular bag distort the natural lens in order to change its power and/or the location of the lens, so that the eye can focus on objects at varying distances away from the eye in a process known as accommodation.

For some people suffering from cataracts, the natural lens of the eye becomes clouded or opaque. If left untreated, the vision of the eye becomes degraded and blindness can occur in the eye. A standard treatment is surgery, during which the natural lens is broken up, removed, and replaced with a manufactured intraocular lens. Typically, the capsular bag is left intact in the eye, so that it may house the implanted intraocular lens.

Because the capsular bag is capable of motion, initiated by the ciliary muscle and/or zonules, it is desirable that the implanted intraocular lens change its power and/or location in the eye in a manner similar to that of the natural lens. Such an accommodating lens may produce vastly improved vision over a lens with a fixed power and location that does not accommodate.

Figure 1:
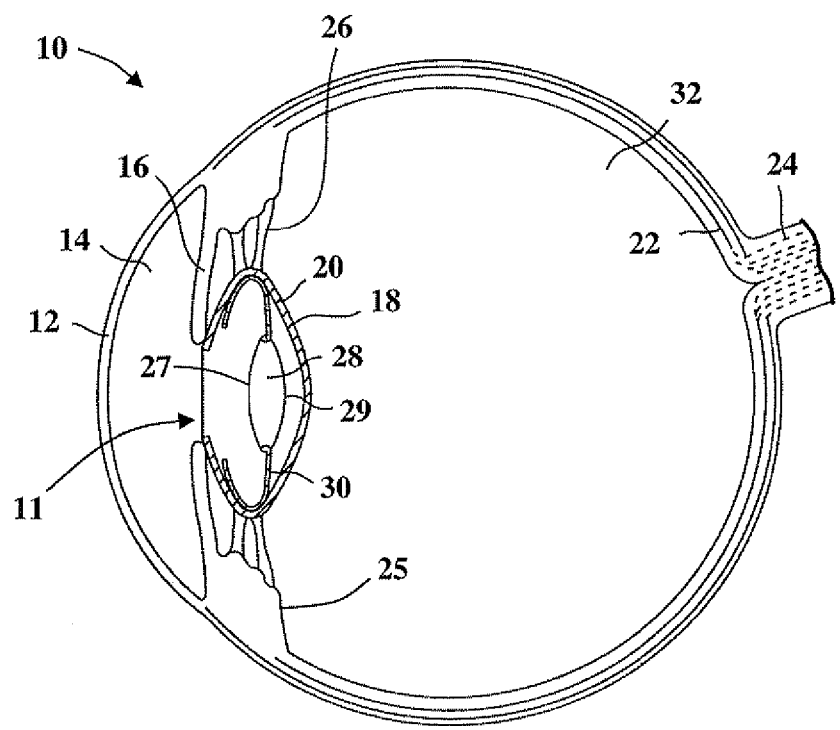
FIG. 1 is a plan drawing of a human eye having an implanted intraocular lens, in an accommodative or "near" state.

FIG. 1 shows a human eye 10, after an accommodating intraocular lens has been implanted. Light enters from the left of FIG. 1, and passes through the cornea 12, the anterior chamber 14, the iris 16, and enters the capsular bag 18. Prior to surgery, the natural lens occupies essentially the entire interior of the capsular bag 18. After surgery, the capsular bag 18 houses the intraocular lens, in addition to a fluid that occupies the remaining volume and equalizes the pressure in the eye. The intraocular lens is described in more detail below. After passing through the intraocular lens, light exits the posterior wall 20 of the capsular bag 18, passes through the posterior chamber 32, and strikes the retina 22, which detects the light and converts it to a signal transmitted through the optic nerve 24 to the brain.

A well-corrected eye forms an image at the retina 22. If the lens has too much or too little power, the image shifts axially along the optical axis away from the retina, toward or away from the lens. Note that the power required to focus on a close or near object is more than the power required to focus on a distant or far object. The difference between the "near" and "far" powers is known typically as the range of accommodation. A normal range of accommodation is about 4 diopters, which is considered sufficient for most patients.

The capsular bag is acted upon by the ciliary muscle 25 via the zonules 26, which distort the capsular bag 18 by stretching it radially in a relatively thick band about its equator. Experimentally, it is found that the ciliary muscle 25 and/or the zonules 26 typically exert a total ocular force of up to about 10 grams of force, which is distributed generally uniformly around the equator of the capsular bag 18. Although the range of ocular force may vary from patient to patient, it should be noted that for each patient, the range of accommodation is limited by the total ocular force that can be exert. Therefore, it is highly desirable that the intraocular lens be configured to vary its power over the full range of accommodation, in response to this limited range of ocular forces. In other words, it is desirable to have a relatively large change in power for a relatively small driving force.

Because the zonules' or ocular force is limited, it is desirable to use a fairly thin lens, compared to the full thickness of the capsular bag. In general, a thin lens may distort more easily than a very thick one, and may therefore convert the ocular force more efficiently into a change in power. In other words, for a relatively thin lens, a lower force is required to cover the full range of accommodation.

Note that there may be an optimum thickness for the lens, which depends on the diameter of the optic. If the lens is thinner than this optimum thickness, the axial stiffness becomes too high and the lens changes power less efficiently. In other words, if the edge thickness is decreased below its optimal value, the amount of diopter power change for a given force is decreased. For instance, for an optic having a diameter of 4.5 mm, an exemplary ideal edge thickness may be about 1.9 mm, with edge thicknesses between about 1.4 mm and about 2.4 having acceptable performance as well.

Note that the lens may be designed so that its relaxed state is the "far" condition (sometimes referred to as "disaccommodative biased"), the "near" condition ("accommodative biased"), or some condition in between the two.

The intraocular lens itself generally has two components: an optic 28, which is made of a transparent, deformable and/or elastic material, and a haptic 30, which holds the optic 28 in place and mechanically transfers forces on the capsular bag 18 to the optic 28. The haptic 30 may have an engagement member with a central recess that is sized to receive the peripheral edge of the optic 28.

When the eye 10 focuses on a relatively close object, as shown in FIG. 1, the zonules 26 relax and the capsular bag 18 returns to its natural shape in which it is relatively thick at its center and has more steeply curved sides. As a result of this action, the power of the lens increases (i.e., one or both of the radii of curvature can decrease, and/or the lens can become thicker, and/or the lens may also move axially), placing the image of the relatively close object at the retina 22. Note that if the lens could not accommodate, the image of the relatively close object would be located behind the retina, and would appear blurred.

Figure 2:
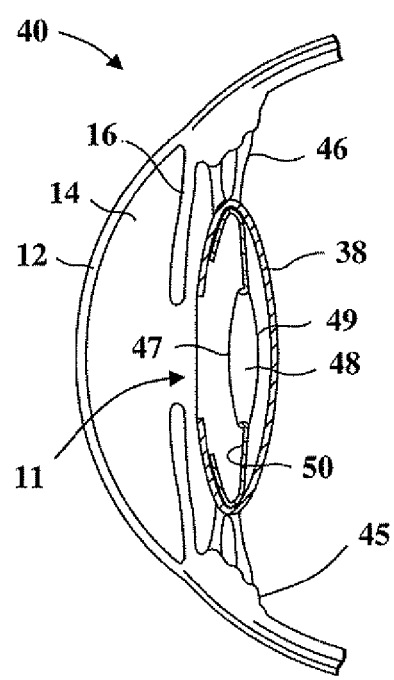
FIG. 2 is a plan drawing of the human eye of FIG. 1, in a disaccommodative or "far" state.

FIG. 2 shows a portion of an eye 40 that is focused on a relatively distant object. The cornea 12 and anterior chamber 14 are typically unaffected by accommodation, and are substantially identical to the corresponding elements in FIG. 1. To focus on the distant object, the ciliary muscle 45 contracts and the zonules 46 retract and change the shape of the capsular bag 38, which becomes thinner at its center and has less steeply curved sides. This reduces the lens power by flattening (i.e., lengthening radii of curvature and/or thinning) the lens, placing the image of the relatively distant object at the retina (not shown).

For both the "near" case of FIG. 1 and the "far" case of FIG. 2, the intraocular lens itself deforms and changes in response to the distortion of the capsular bag. For the "near" object, the haptic 30 compresses the optic 28 at its edge, increasing the thickness of the optic 28 at its center and more steeply curving its anterior face 27 and/or its posterior face 29. As a result, the lens power increases. For the "far" object, the haptic 50 expands, pulling on the optic 48 at its edge, and thereby decreasing the thickness of the optic 48 at its center and less steeply curving (e.g., lengthening one or both radius of curvature) its anterior face 47 and/or its posterior face 49. As a result, the lens power decreases.

Note that the specific degrees of change in curvature of the anterior and posterior faces depend on the nominal curvatures. Although the optics 28 and 48 are drawn as bi-convex, they may also be plano-convex, meniscus or other lens shapes. In all of these cases, the optic is compressed or expanded by essentially forces by the haptic to the edge and/or faces of the optic. In addition, the may be some axial movement of the optic. In some embodiments, the haptic is configured to transfer the generally symmetric radial forces symmetrically to the optic to deform the optic in a spherically symmetric way. However, in alternate embodiments the haptic is configured non-uniformly (e.g., having different material properties, thickness, dimensions, spacing, angles or curvatures), to allow for non-uniform transfer of forces by the haptic to the optic. For example, this could be used to combat astigmatism, coma or other asymmetric aberrations of the eye/lens system. The optics may optionally have one or more diffractive elements, one or more multifocal elements, and/or one or more aspheric elements.

Figure 3:
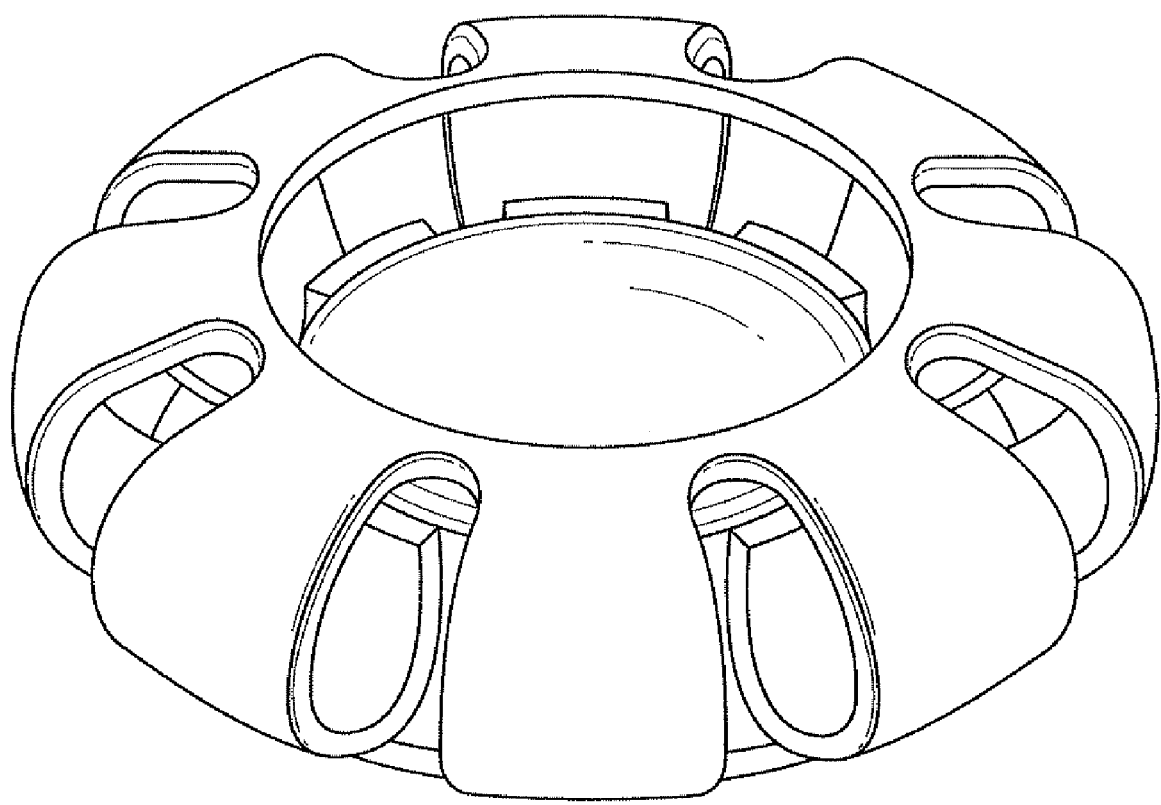
FIG. 3 is an isometric drawing of a haptic coupled to an optic.

FIG. 3 shows a deformable optic with an exemplary haptic, shown in isometric view and removed from the eye. The view of FIG. 3 shows that the haptic extends a full 360 degrees azimuthally around the edge of the optic, which is not seen in the cross-sectional view of FIGS. 1 and 2.

The exemplary haptic of FIG. 3 has various segments or filaments, each of which extends generally in a plane parallel to the optical axis of the lens. For the exemplary haptic of FIG. 3, the segments are joined to each other at one end, extend radially outward until they contact the capsular bag, then extend radially inward until they contact the edge of the optic. At the edge of the optic, the haptic segments may remain separate from each other, as shown in FIG. 3, or alternatively some or all segments may be joined together. Any or all of the width, shape and thickness of the segments may optionally vary along the length of the segments. The haptic may have any suitable number of segments, including but not limited to, 4, 6, 8, 10, 12, 14, and 16.

Note that the region of contact between the optic and the haptic in FIG. 3 extends into the edge of the optic, similar to the interface between a bicycle tire and the rim that holds it in place. This region of contact between the haptic and the optic is described and shown in much greater detail in the text and figures that follow.

Figure 4:
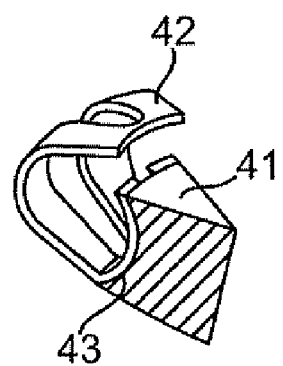
FIG. 4 is a cross-sectional isometric drawing of a haptic segment coupled to an optic segment.

FIG. 4 shows an azimuthal slice of an optic 41 and a haptic 42. Although only two segments of the haptic 42 are shown in FIG. 4, it will be understood that haptic 42 may extend fully around the equator of the optic 41.

Of particular note is the interface between the haptic 42 and the optic 41. The optic 41 in FIG. 4 has an annular recess 43 around its edge, and the haptic 42 extends or protrudes into this annular recess, instead of merely contacting the optic at a cylindrical edge parallel to the optical axis.

This protrusion into the edge of the optic may allow for greater transfer of forces from the capsular bag, through the haptic, to the optic. There may be a greater coupling of these forces to the anterior and/or posterior surfaces of the optic, which may result in more distortion or deforming of these surfaces for a given distorting force. As a result, the limited capsular bag force may produce a greater distortion of the optic, and, therefore, a larger change in power and/or a larger axial translation of the image at the retina.

The optic 41 is made from a relatively soft material, so that it can distort or change shape readily under the limited deforming force initiated by the capsular bag and transmitted through the haptic 42. An exemplary material is a relatively soft silicone material, although other suitable materials may be used as well. The stiffness of the optic 41 may be less than 500 kPa, or preferably may be between 0.5 kPa and 500 kPa, or more preferably may be between 25 kPa and 200 kPa, or even more preferably may be between 25 kPa and 50 kPa.

In contrast with the optic 41, the haptic 42 is made from a relatively stiff material, so that it can efficiently transmit the deforming forces from the capsular bag to the optic 41. An exemplary material is a relatively stiff silicone material, although other suitable materials may be used as well, such as acrylic, polystyrene, or clear polyurethanes. The haptic 42 may preferably be stiffer than the optic 41. The stiffness of the haptic 42 may be greater than 500 kPa, or preferably may be greater than 3000 kPa.

Because the haptic 42 extends into the optic 41 in a region around its circumference, it also may extend into the clear aperture of the optic 41. For this reason, the haptic may preferably be transparent or nearly transparent, so that it does not substantially block any light transmitted through the lens.

In addition, it is desirable that the interface between the optic 41 and the haptic 42 does not produce any significant reflections, which would produce scattered light within the eye, and would appear as a haze to the patient. A convenient way to reduce the reflections from the interface is to match the refractive indices of the haptic and the optic to each other.

A simple numerical example shows the effect of mismatch of refractive indices on reflected power. For a planar interface at normal incidence between air (refractive index of 1) and glass (refractive index of 1.5), 4% of the incident power is reflected at the interface. For such an interface between air and glass, there is no attempt to match refractive indices, and this 4% reflection will merely provide a baseline for comparison. If, instead of 1 and 1.5, the refractive indices differ by 4%, such as 1.5 and 1.56 or 1.5 and 1.44, there is a 0.04% reflection, or a factor of 100 improvement over air/glass. Finally, if the refractive indices differ by only 0.3%, such as 1.5 and 1.505 or 1.5 and 1.495, there is a 0.00028% reflection, or a factor of over 14000 improvement over air/glass. In practice, tolerances such as the 0.3% case may be achievable, and it is seen that a negligible fraction of power may be reflected at the interface between a haptic and an optic whose refractive indices differ by 0.3%. Note that the above base value of 1.5 was chosen for simplicity, and that the haptic and optic may have any suitable refractive index.

It is desirable that the refractive indices of the haptic and optic be essentially the same. For the purposes of this document, "essentially the same" may mean that their refractive indices are equal to each other at a wavelength within the visible spectrum (i.e., between 400 nm and 700 nm). Note that the haptic and optic may optionally have different dispersions, where the refractive index variation, as a function of wavelength, may be different for the haptic and the optic. In other words, if the refractive indices of the haptic and optic are plotted as a function of wavelength, they may or may not have different slopes, and if the two curves cross at one or more wavelengths between 400 nm and 700 nm, then the refractive indices may be considered to be essentially the same or essentially equal.

The exemplary haptic 42 has segments that are not joined at the edge of the optic 41, and has a generally uniform thickness throughout. Note that these two qualities of the haptic may be varied, as shown in FIGS. 5 through 8.

Figure 5:
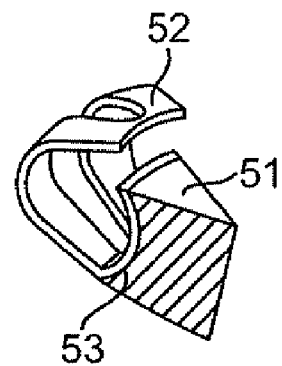
FIG. 5 is a cross-sectional isometric drawing of a haptic segment coupled to an optic segment.

In FIG. 5, the segments of the haptic 52 are joined at the edge of the optic 51. The optic has an annular recess 53, analogous to annular recess 43 of FIG. 4. Note that at the edge of the optic, the haptic segments need not be all joined or all separate, but may be joined in adjacent pairs or in any other suitable scheme.

Figure 6:
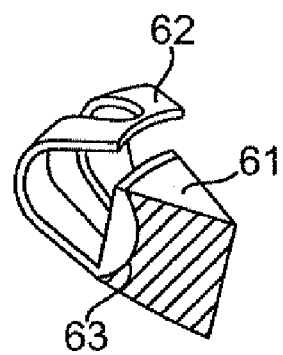
FIG. 6 is a cross-sectional isometric drawing of a haptic segment coupled to an optic segment.

In FIG. 6, the haptic 62 has a variation in thickness along the edge of the optic 61, so that the side opposite the annular recess 63 is essentially flat.

Figure 7:
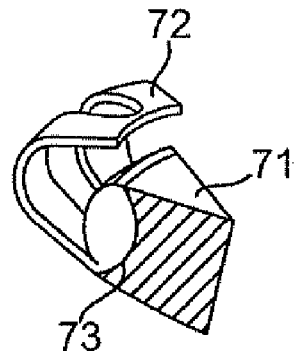
FIG. 7 is a cross-sectional isometric drawing of a haptic segment coupled to an optic segment.

In FIG. 7, the haptic 72 has a variation in thickness along the edge of the optic 71, so that the side opposite the annular recess 73 is convex.

Figure 8:
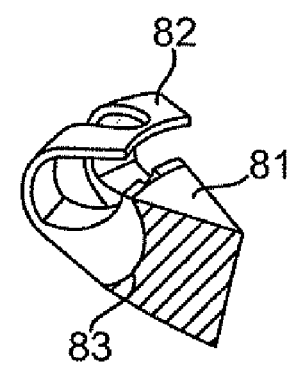
FIG. 8 is a cross-sectional isometric drawing of a haptic segment coupled to an optic segment.

In FIG. 8, the haptic 82 has an increasing thickness approaching the annular recess 83 of the optic 81.

In FIGS. 4 through 8, each haptic is made from a single, relatively stiff material, and each optic is made from a single, relatively soft material. As an alternative, other materials having different stiffnesses may be introduced.

Figure 9:
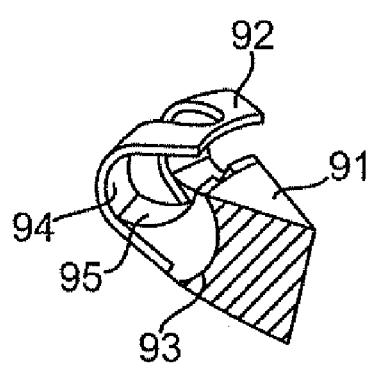
FIG. 9 is a cross-sectional isometric drawing of a haptic segment coupled to an optic segment.

For instance, FIG. 9 shows an optic 91 made from a soft material, a haptic 92 made from a stiff material 94, and a third material 95 that is stiffer than the haptic stiff material 94. Alternatively, the third material 95 may be less stiff than the haptic stiff material 94. In this example, the third material 95 is in contact with the optic 91 at its annular recess 93. For the purposes of this document, such a third material 95 may be considered to be part of the haptic 92, although in practice it may optionally be manufactured as part of the optic 91. Alternatively, there may be one or more materials used for the haptic and/or the optic, which may have the same or different stiffnesses.

In FIGS. 4 through 9, each optic has an annular recess with a generally smooth, curved, concave profile, along a direction parallel to the optical axis of the lens. (Similarly, each corresponding haptic has a generally smooth, curved, convex profile, along a direction parallel to the optical axis of the lens.) As an alternative, the profile need not be generally smooth, and/or need not be curved.

Figure 10:
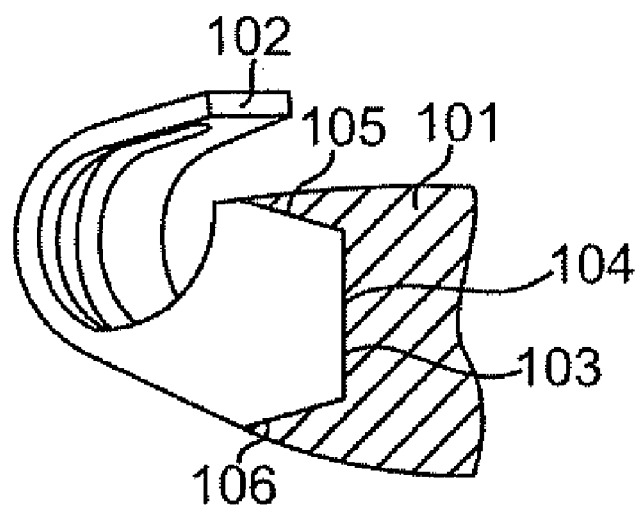
FIG. 10 is a cross-sectional isometric drawing of a haptic segment coupled to an optic segment.

For instance, the optic 101 of FIG. 10 has an annular recess 103 with a concave profile that is not smooth but has corners, and is not curved but has straight portions. (Similarly, the haptic 102 has a convex profile with corners and straight portions.) In this case, one of the straight portions 104 is parallel to the optical axis of the lens, and the other two straight portions 105 and 106 are inclined with respect to a plane perpendicular to the optical axis.

In FIG. 10, the deepest portion of the profile falls along the straight portion 103, although it may fall at a particular point rather than along a full line. The particular point may be a corner, or may be a point along a smooth curve. For FIG. 10, the deepest portion passes through the midpoint of the lens (i.e., the plane halfway between the anterior and posterior surfaces of the optic).

Figure 11:
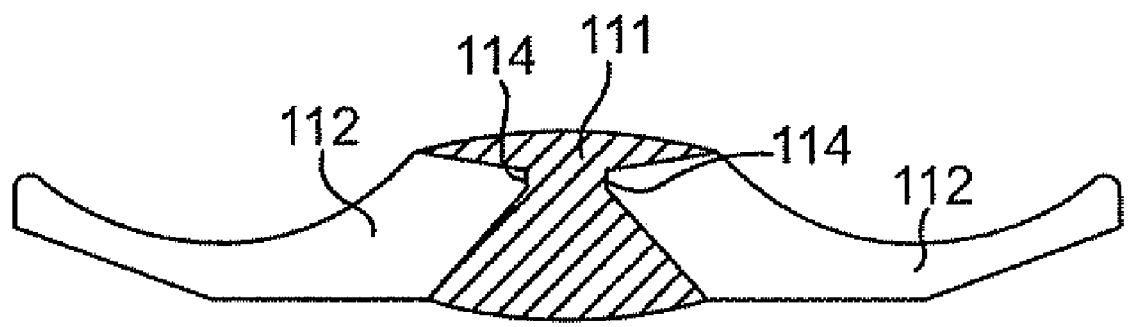
FIG. 11 is a cross-sectional plan drawing of a haptic segment coupled to an optic segment.

As an alternative, the deepest portion of the profile may be located away from the midpoint of the lens, and may be located closer to either the anterior or posterior surfaces of the optic. For instance, FIG. 11 shows a cross-section of an optic 111 and a portion of a haptic with such an asymmetric deepest portion 114. A potential advantage of such asymmetry is that the deformation of the surfaces may be tailored more specifically than with a symmetric profile, so that one surface may deform more than the other under a deforming force exerted by the haptic. This may be desirable for particular optic shapes.

In FIGS. 4 through 10, each of the haptics is attached to the optic at only one end. As an alternative, the haptic may be attached to the optic at both ends. For instance, haptic 272 of FIG. 27 attaches to optic 271 at both ends. Optic 271 has annular recess 273, analogous with the annular recesses of FIGS. 4 through 11. Furthermore, the interior region of the haptic, shown as hollow in FIG. 27, may optionally be filled with a liquid or a gel having particular mechanical properties.

Figure 27:
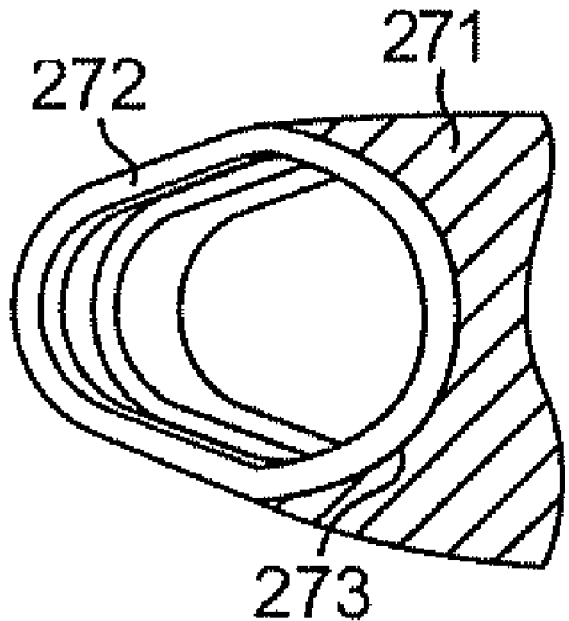
FIG. 27 is a cross-sectional isometric drawing of a haptic segment coupled to an optic segment.
Figure 28:
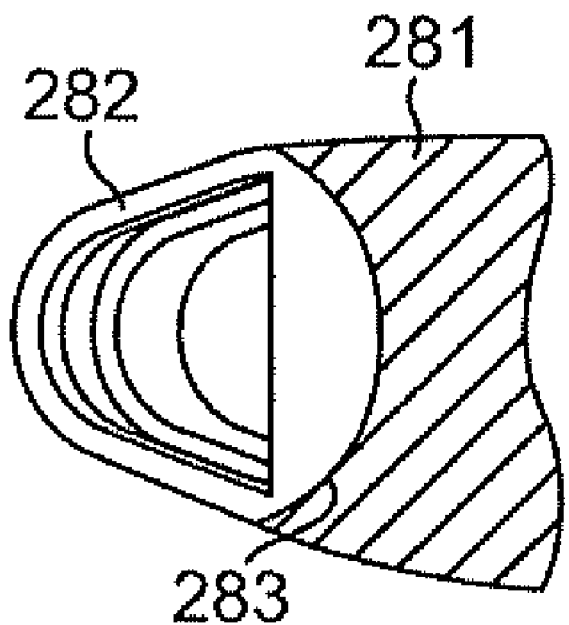
FIG. 28 is a cross-sectional isometric drawing of a haptic segment coupled to an optic segment.

FIG. 28 shows a haptic 282 similar to that in FIG. 27, but with a variation in thickness in the region opposite the annular recess 283 of the optic 281. Similarly, the thickness may optionally be varied at any point on the haptic 282.

Figure 29:
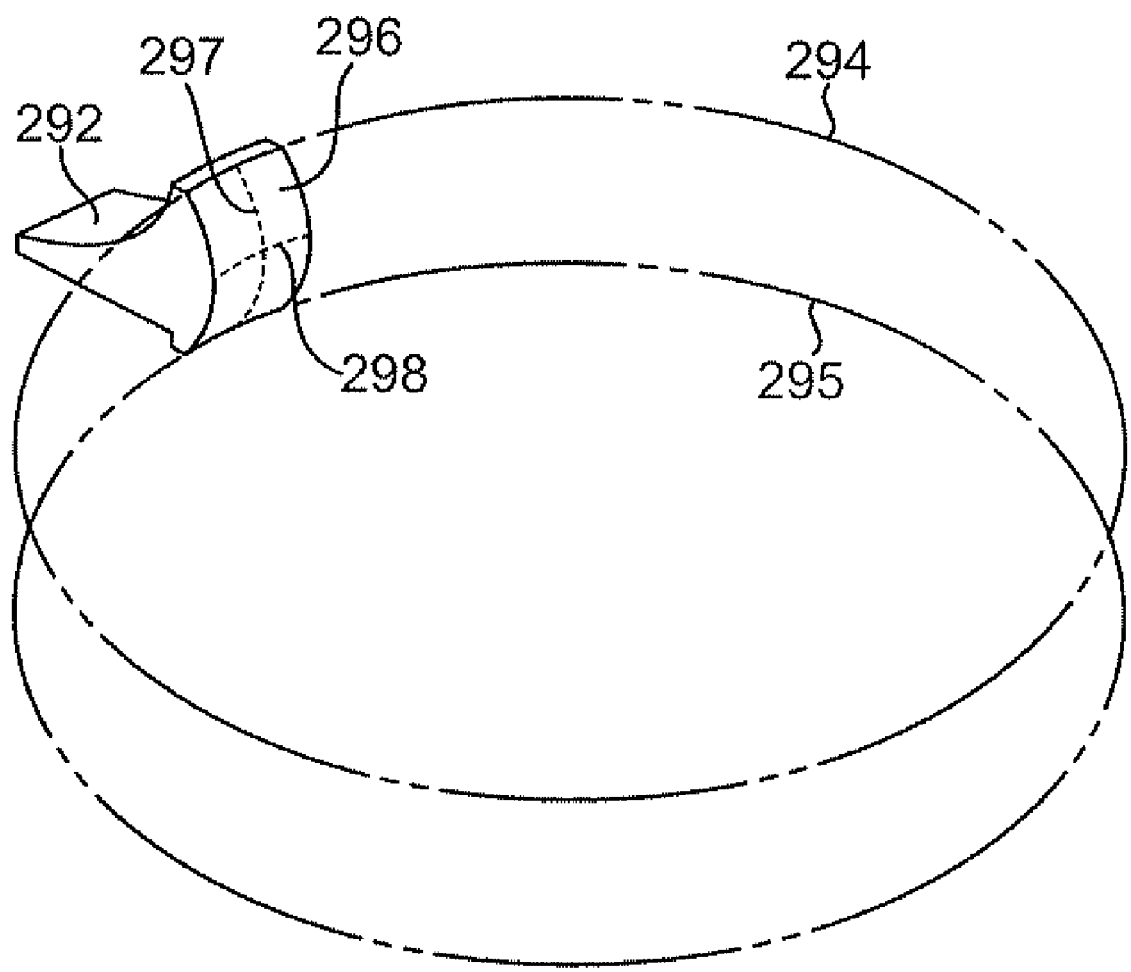
FIG. 29 is a isometric drawing of the geometry of a saddle-shaped haptic.

For further clarification of the previous geometries, FIG. 29 shows a small portion of a haptic 292 along with some geometrical constructs. In FIG. 29, the optical axis of the lens is vertical. The upper ellipse 294 corresponds to the circumference of the anterior (or posterior) surface of the lens, and the lower ellipse 295 corresponds to the circumference of the posterior (or anterior) surface of the lens. The haptic 292 has a portion 296 that may be considered saddle-shaped or hyperbolic, with a convex profile 297 along a direction parallel to the optical axis of the lens, and a concave profile 298 in a plane perpendicular to the optical axis of the lens. Similarly, the optic (not shown) would have a corresponding annular recess that contacts a portion 296 of the haptic. Although the convex profile 297 and concave profile 298 are shown as smooth and continuous curves, they may alternatively have one or more straight segments, and/or may alternatively be asymmetric with respect to the anterior or posterior surfaces of the optic.

It may be beneficial to describe in words the interface between the haptic and the optic for the various lenses shown in the figures. Consider a radial plane to be a plane that includes the optical axis of the lens. The intersection of the radial plane with the haptic/optic interface of the lens forms a so-called "cross-sectional curve." The endpoints of the cross-sectional curve are to be referred to as anterior and posterior endpoints, respectively.

As seen from the figures, the cross-sectional curve protrudes into the optic. We may define this protrusion more precisely by comparing the cross-sectional curve with a so-called "cylindrical edge" of the optic, which is taken to be a line connecting the anterior and posterior endpoints of the cross-sectional curve. Note that this "cylindrical edge" need not be truly parallel to the optical axis. "Protrusion into the optic" may therefore be interpreted in any or all of the following manners:

(1) The separation between the cross-sectional curve and the optical axis is less than the separation between the cylindrical edge and the optical axis, for all points between the anterior and posterior endpoints. This includes the designs of FIGS. 4-11, 27 and 28, and includes additional designs in which the entire cross-sectional curve protrudes into the optic.

(2) The separation between the cross-sectional curve and the optical axis is less than the separation between the cylindrical edge and the optical axis, for at least one point between the anterior and posterior endpoints. This also includes the designs of FIGS. 4-11, 27 and 28, but may include additional designs in which only a portion of the cross-sectional curve protrudes into the optic.

As also seen from the figures, the cross-sectional curve may take on various shapes. For all of the designs shown in the figures, the cross-sectional curve extends inward toward the optical axis as one moves away from the anterior endpoint, reaches a "local minimum" or a "deepest portion" at which the cross-sectional curve is at its closest to the optical axis, then extends outward away from the optical axis as one approaches the posterior endpoint. Differences arise among the various designs in the character and location of the deepest portion, as well as the local curvature of the cross-sectional curve. Three such categories of differences are detailed below; these three categories are not intended to be all-inclusive.

(1) The cross-sectional curve does not contain any corners, discontinuities, or straight segments. This includes the designs of FIGS. 4-9, 27 and 28. Note that the "deepest portion" occurs at only one point along the cross-sectional curve. This category of curve may be referred to as a "continuous curve". Note that a continuous curve may optionally extend in part outside the so-called "cylindrical edge" of the optic; the designs shown in the figures extend only into the cylindrical edge of the optic.

(2) The cross-sectional curve may contain at least one straight segment, but does not contain any corners or discontinuities. The straight segment may be located anywhere along the cross-sectional curve. The straight segment may be inclined with respect to the optical axis, or may be parallel to the optical axis. The straight segment may also be parallel to the optical axis at the "deepest portion," so that the deepest portion may have a finite spatial extent, rather than a single location.

(3) The cross-sectional curve may contain at least one straight segment, and may contain at least one corner, but does not contain any discontinuities. This includes the designs of FIGS. 10 and 11, which each contain three straight segments and two corners. In each of the designs of FIGS. 10 and 11, as one moves away from the anterior endpoint, the cross-section curve contains a straight segment extending toward the optical axis, followed by a straight segment parallel to the optical axis, followed by a straight segment extending away from the optical axis as one approaches the posterior endpoint. For the designs of FIGS. 10 and 11, the middle straight segment is the "deepest portion" of the curve, which is bounded on both sides by a segment that is inclined with respect to the optical axis and is also inclined with respect to both the anterior and posterior surfaces of the optic. In FIG. 10, the middle portion 104 is bounded on either side by straight portions 105 and 106, and is symmetrically located between the anterior and posterior surfaces. In FIG. 11, the middle portion 114 is also bounded by straight portions, but is asymmetrically located between the anterior and posterior surfaces.

The following paragraphs describe a series of simulation results that compare the performance of the haptic designs of FIGS. 4-8 to each other and to a baseline design.

A series of finite element calculations were performed, each with identical materials, identical shapes for the optic, identical shapes for the annular recess in the optic, and identical shapes for the haptic portion that contacts the capsular bag of the eye. The haptic thickness was varied to correspond to the cases of FIGS. 4 through 8. Finally a baseline case was calculated, in which the convex profile (analogous to element 297 in FIG. 29) was not convex, but was planar; in this baseline case, the haptic did not protrude or extend into the edge of the adjustable optic. The haptic thickness of the baseline case was the same as for FIG. 4.

The results of the calculations are expressed as a power change in diopters, where a larger number is better. The baseline case produced a power change of 2.94 diopters. The configuration of FIG. 4 produced a power change of 5.24 diopters. The configuration of FIG. 5 produced a power change of 4.99 diopters. The configuration of FIG. 6 produced a power change of 4.96 diopters. The configuration of FIG. 7 produced a power change of 5.62 diopters. The configuration of FIG. 8 produced a power change of 9.24 diopters. These power change values are all greater than the baseline case, and all exceed the 4 diopter value that is generally accepted as a full range of accommodation.

Figure 12:
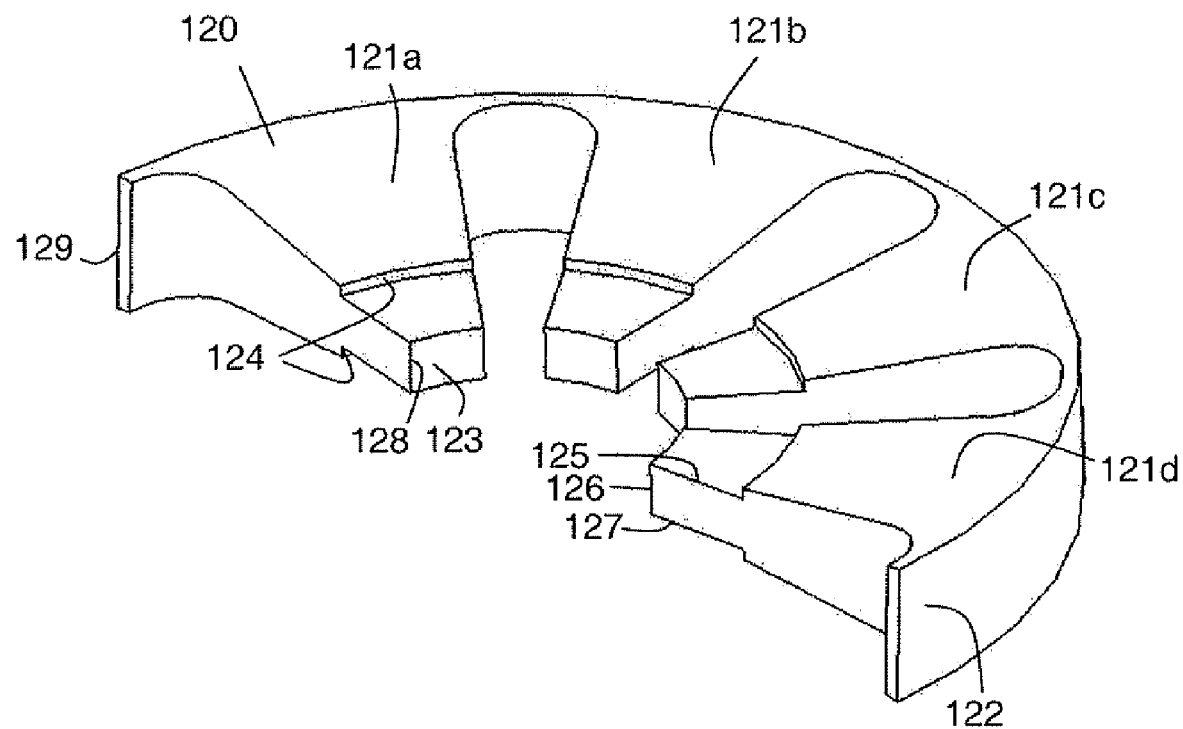
FIG. 12 is a cross-section drawing of a haptic.
Figure 13:
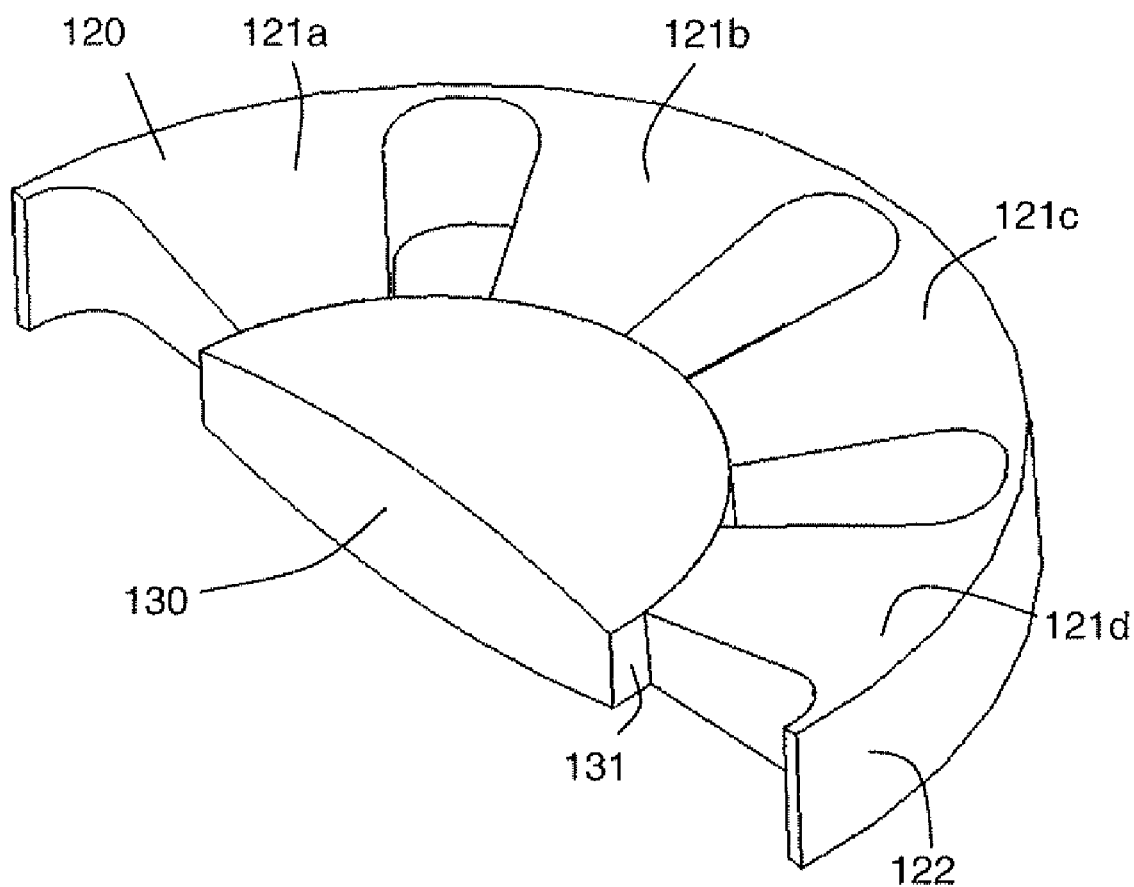
FIG. 13 is a cross-sectional drawing of the haptic of FIG. 12, with an optic.
Figure 14:
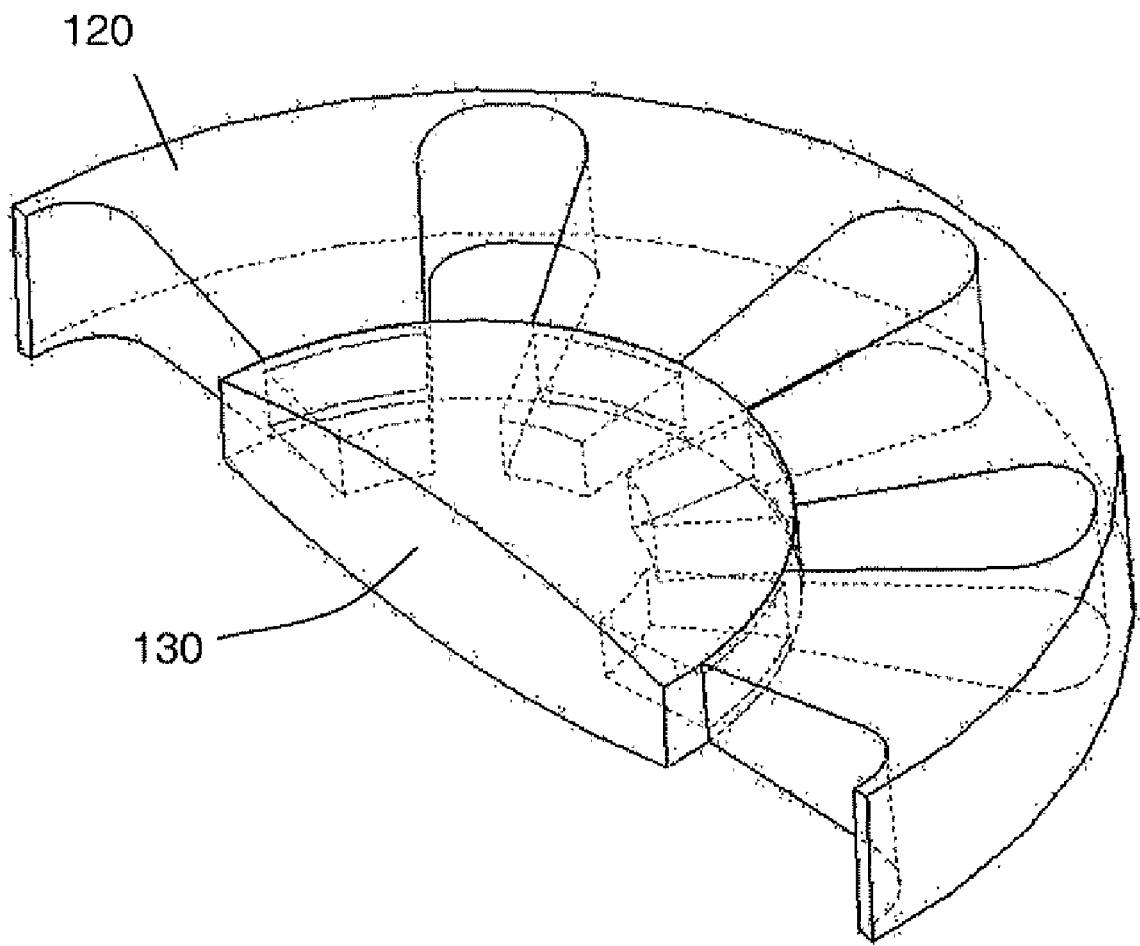
FIG. 14 is the cross-section drawing of the haptic and optic of FIG. 13, with additional hidden lines.
Figure 15:
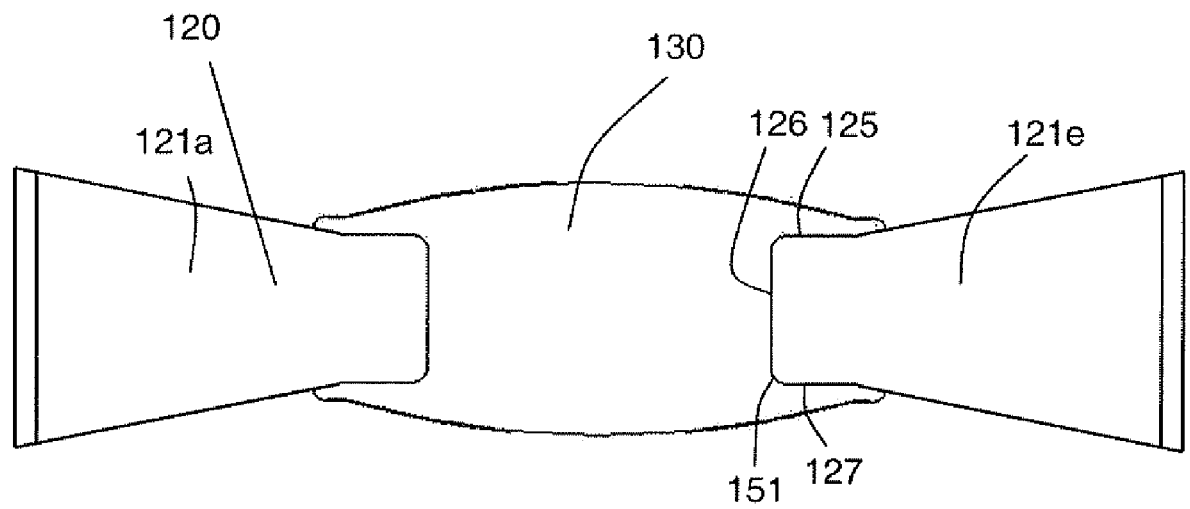
FIG. 15 is an end-on cross-sectional drawing of the haptic and optic of FIG. 13.
Figure 16:
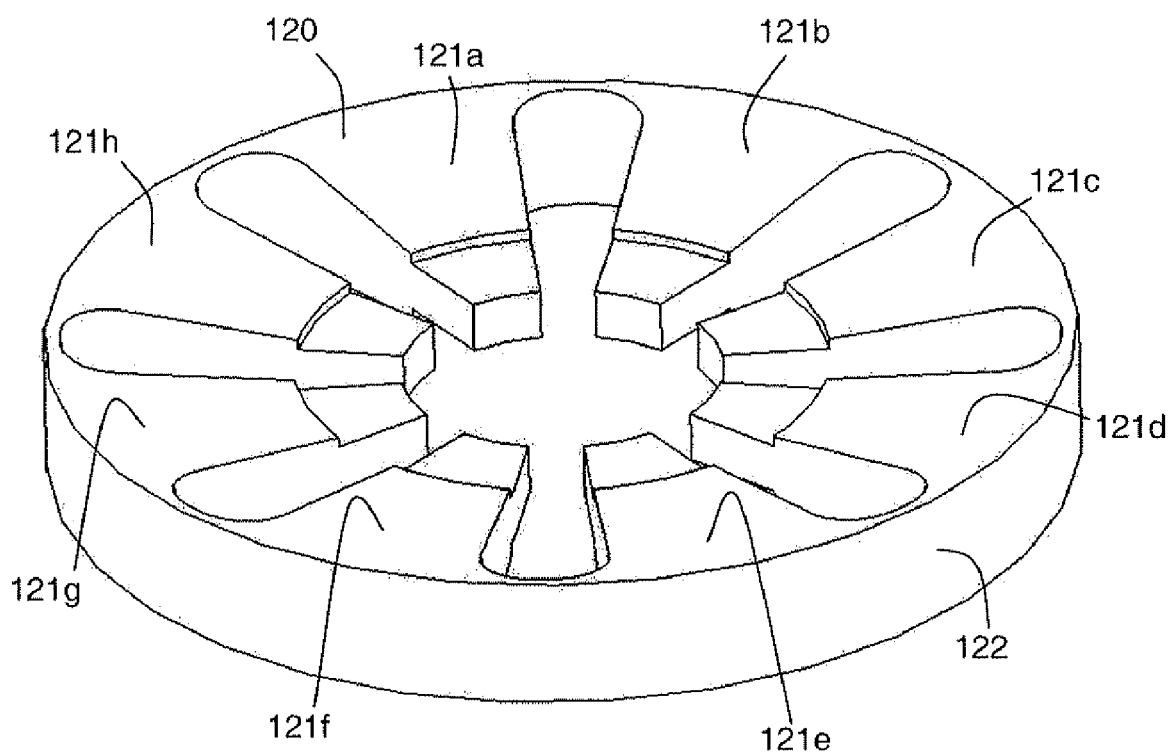
FIG. 16 is a plan drawing of the haptic of FIG. 12.
Figure 17:
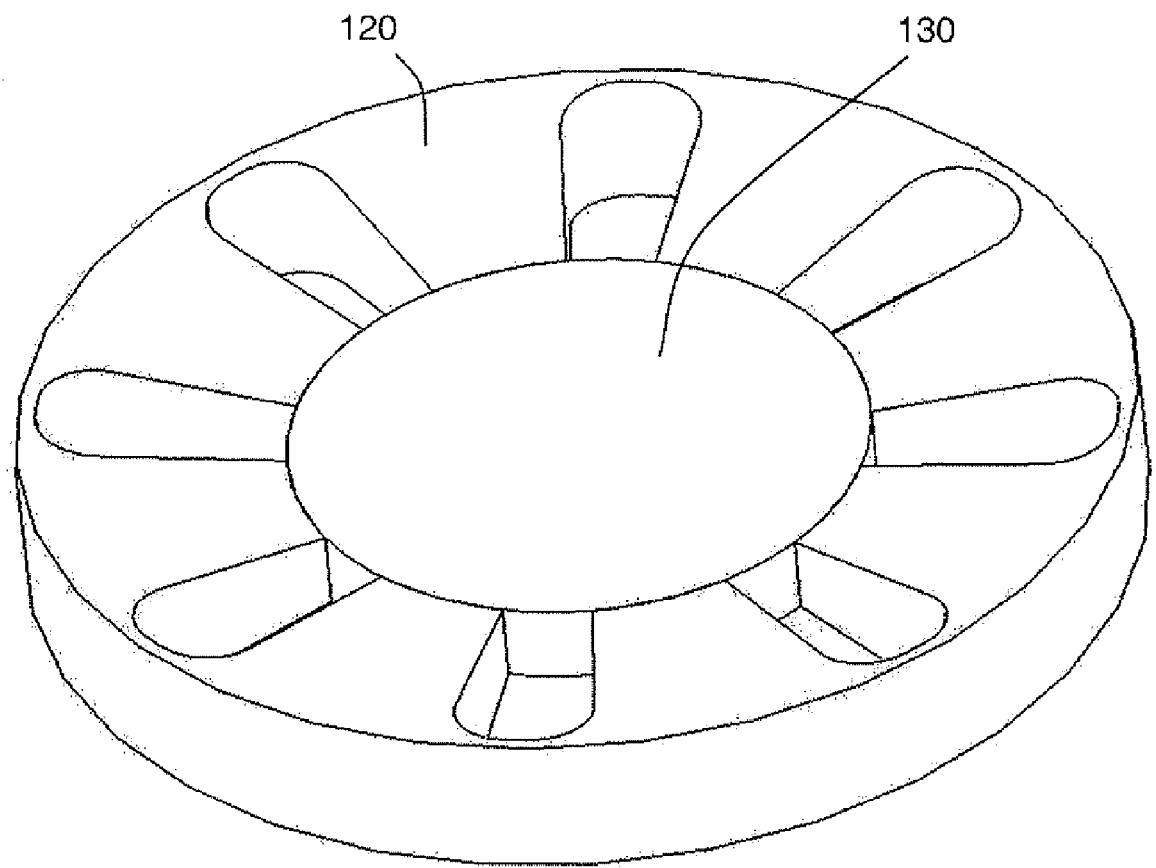
FIG. 17 is a plan drawing of the haptic of FIG. 16, with an optic.
Figure 18:
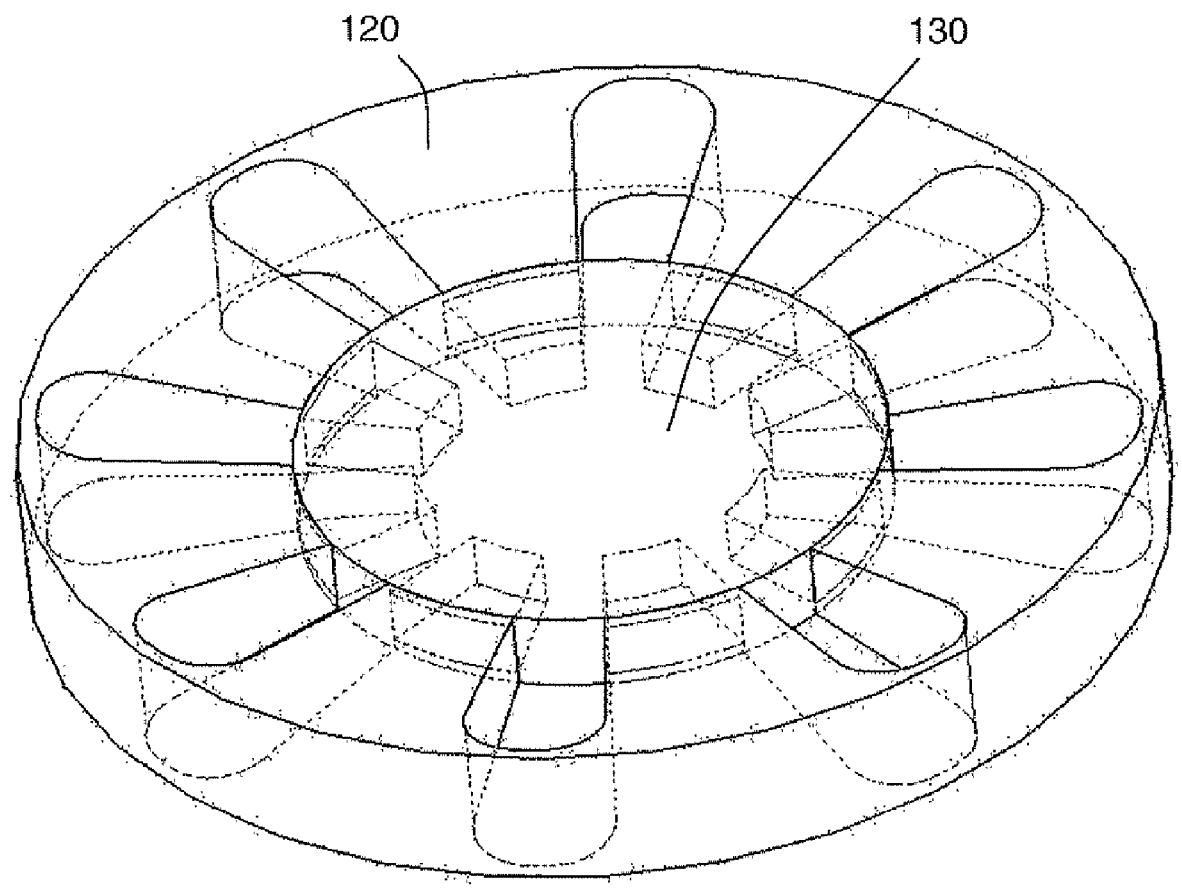
FIG. 18 is the cross-section drawing of the haptic and optic of FIG. 17, with additional hidden lines.

FIGS. 12 through 18 show an exemplary haptic 120 in various plan and cross-sectional views, both with and without an optic 130. FIG. 12 is a cross-section drawing of a haptic 120. FIG. 13 is a cross-sectional drawing of the haptic of FIG. 12, with an optic 130. FIG. 14 is the cross-section drawing of the haptic 120 and optic 130 of FIG. 13, with additional hidden lines. FIG. 15 is an end-on cross-sectional drawing of the haptic 120 and optic 130 of FIG. 13. FIG. 16 is a plan drawing of the haptic 120 of FIG. 12. FIG. 17 is a plan drawing of the haptic 120 of FIG. 16, with an optic 130. FIG. 18 is the cross-section drawing of the haptic 120 and optic 130 of FIG. 17, with additional hidden lines.

The haptic 120 of FIGS. 12 through 18 has eight filaments denoted by elements 121a through 121h. Alternatively, the haptic 120 may have more or fewer than eight filaments (e.g., 3 filaments, 4 filaments, or 16 filaments). The filaments 121a-h may be connected at their outermost edge and may be unconnected at their innermost edge.

Note that the filaments 121a-h may vary in size along their lengths, from the innermost edge 123 to the ends of the filament adjacent to the outermost edge 122 of the haptic 120. In particular, the filaments 121a-h may increase in cross-sectional dimensions with radial distance away from the center of the lens. In a direction parallel to the optical axis (vertical in FIG. 12), the outermost extent of the haptic filaments, denoted by length 129, may be larger than the innermost extent of the haptic filaments, denoted by dimension 128. Alternatively, the length 129 may be equal to or less than length 128. Similarly, in a direction perpendicular to the optical axis (essentially in the plane of the lens), the filaments may be effectively wedge-shaped, with a greater radial extent at the outer edge than at the inner edge. The cross-section of each filament may be symmetric with respect to the plane of the lens, as shown in FIG. 12. Alternatively, the cross-section of one or more filaments may be asymmetric with respect to the plane of the lens, with differing amounts of material on anterior and posterior sides of the filament.

The outermost edge 122 of the haptic 120 mechanically couples the intraocular lens to the capsular bag of the eye. The haptic 120 may receive an optic 130 in its central region, which may be molded directly onto the haptic 120. Alternatively, the optic may be manufactured separately from the haptic, then attached to the haptic.

The haptic 120 may have an optional lip or ridge 124 on one or both of the anterior and posterior faces, so that if an optic is molded directly onto the haptic 120, the optic resides in the central portion of the haptic within the lip 124. The lip 124 may be circularly symmetric on both faces of the haptic, as shown in FIGS. 12 through 18. Alternatively, the lip 124 may have a different radius on one or more filaments, so that optic material may extend out different radial distances along particular filaments. As a further alternative, the lip 124 may have different radii on the anterior and posterior faces of the haptic 120.

Once the optic 130 is formed on, attached to, or placed within the haptic 120, the haptic 120 protrudes into the edge 131 of the optic 130. For the specific design of FIGS. 12 through 18, portions of each filament 121a-h extend into the edge 131 of the optic 130, with the anterior and posterior faces of the optic 130 surrounding and/or encompassing the haptic filaments 121a-h in the central portion demarcated by the lip 124.

For a cross-section of the filaments 121a-h, taken in a plane parallel to the optical axis of the lens (vertical in FIGS. 12 through 18), the cross-section has a particular profile that extends into the edge 131 of the optic 130. The profile may contain one or more straight and/or curved portions, and may have a deepest portion at one or more points or along a straight segment. For instance, the profile in FIGS. 12 and 15 has a generally straight portion 125 extending generally radially inward, followed by a generally straight portion 126 extending generally parallel to the optical axis, followed by a generally straight portion 127 extending generally radially outward. The generally straight portions 125, 126 and 127 may optionally have one or more rounded portions 151 between them. Straight portions 125 and 127 may be generally parallel to each other, or may be generally inclined with respect to each other. The generally straight portion 126 may be generally parallel to the optical axis, as in FIGS. 12 and 15, or may alternatively be inclined with respect to the optical axis. The deepest portion of the profile of FIGS. 12 and 15 may be the straight portion 126. The profile made up of segments 125, 126 and 127 shown in FIGS. 12 and 15 may be generally convex in a direction parallel to the optical axis of the lens.

Referring to FIG. 15, the axial thickness (i.e., along an axis parallel to the optical axis passing through the center of the optic 130) of the portions of the haptic 120 disposed within the optic 130 may be selected to control the amount and/or distribution of an ocular force acting on the intraocular lens 240. For example, in some embodiments, the performance (e.g., the change Diopter power of the optic 130 between accommodative and disaccommodative configurations) increases as the edge thickness increases. In such embodiments, other design constraints (e.g., optical performance or physical constraints of the eye) may, however, place an upper limit on the maximum optic edge thickness. In some embodiments, the portion of the haptic 120 inside the optic 130 has a maximum axial thickness that is at least one half a maximum axial thickness of the optic 130 along the optical axis, as clearly illustrated in FIG. 15. In other embodiments, the ring portion 246 of the haptic 244 has a maximum axial thickness that is at least 75% of a maximum axial thickness of the central zone. The advantages of the axial thickness the protruding portions of the haptic 120 may also be applied to other embodiments of the invention discussed herein.

In certain embodiments, the optic 130 is a multifocal optic. For example, the portion of the optic 130 between the ends 126 of the haptic 120 may comprise a first zone having a first optical power and the portion of the optic 130 into which the filaments 121 protrude may comprise a second zone having a second optic power that is different from the first optical power. In some embodiments, the optic 130 may change from a monofocal optic to a multifocal optic, depending upon the amount of ocular force on the haptic 120 and/or the state of accommodation of the eye into which the intraocular lens is inserted.

If the optic 130 may be molded directly onto the haptic 120, the haptic 120 may be first expanded or contracted radially by an external force, prior to molding. The optic 130 may then be molded directly onto the expanded or contracted haptic 120. After molding, the external force may be removed, and the haptic may return to its original size or fairly close to its original size, forming radial stresses within the optic 130.

It is desirable that the haptic be made from a stiffer material than the optic, so that any distorting forces induced by the zonules or capsular bag are transmitted efficiently through the haptic to the optic, and efficiently change the shape of the optic. It is also desirable that the haptic and the optic have similar or essentially equal refractive indices, which would reduce any reflections at the interfaces between the haptic and the optic.

Figure 19:
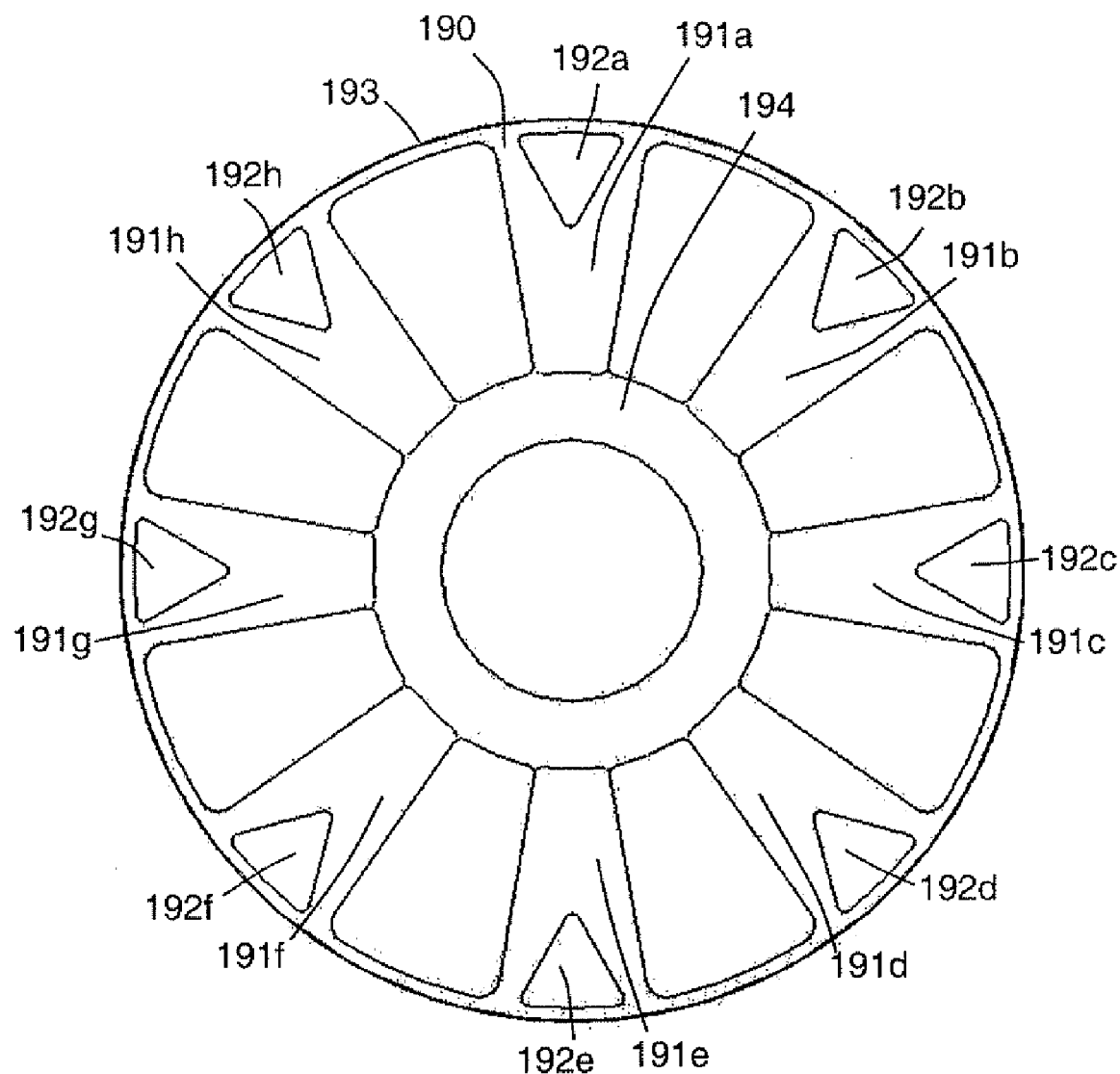
FIG. 19 is a plan drawing of a haptic.
Figure 20:
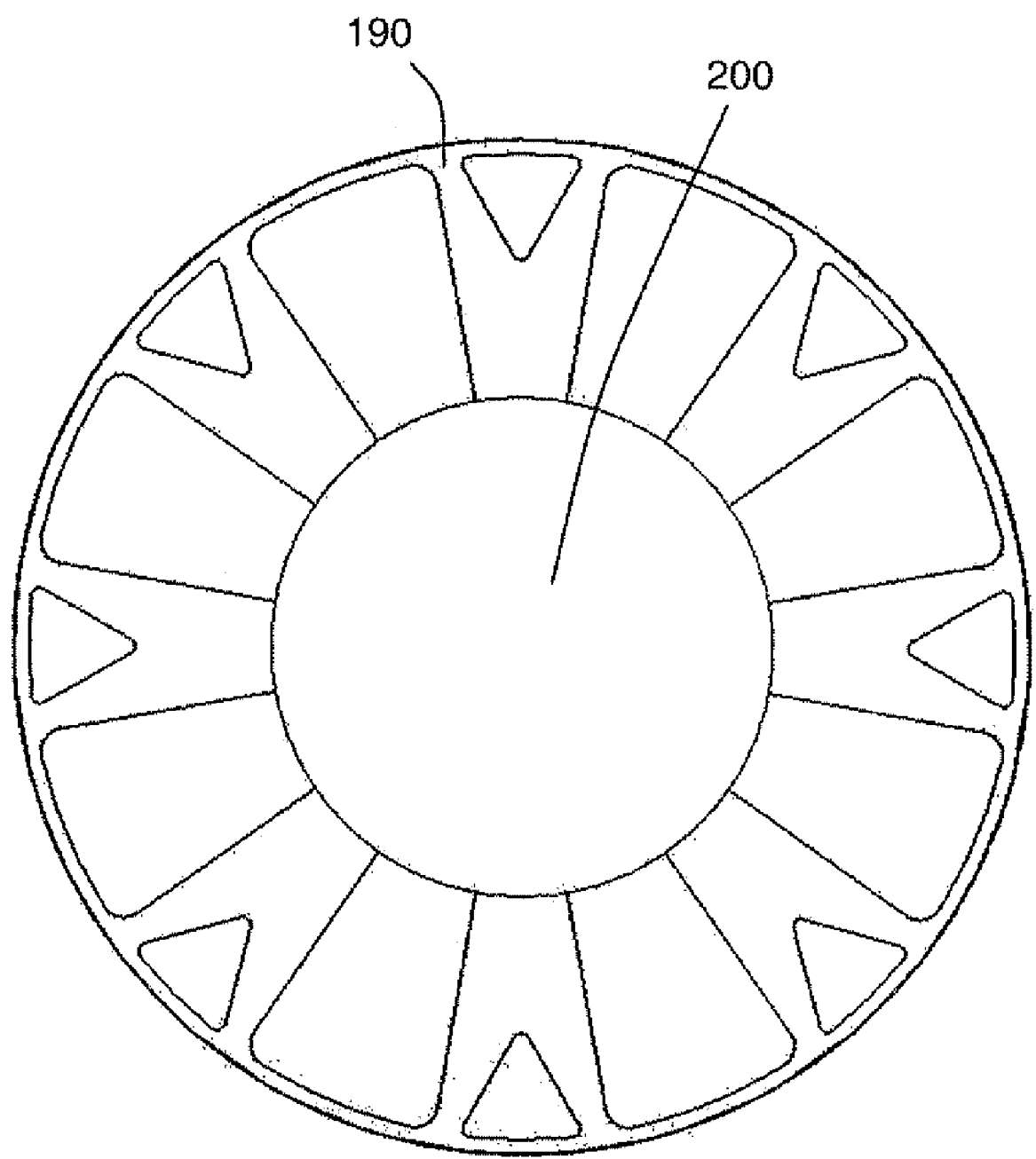
FIG. 20 is a plan drawing of the haptic of FIG. 19, with an optic.
Figure 21:
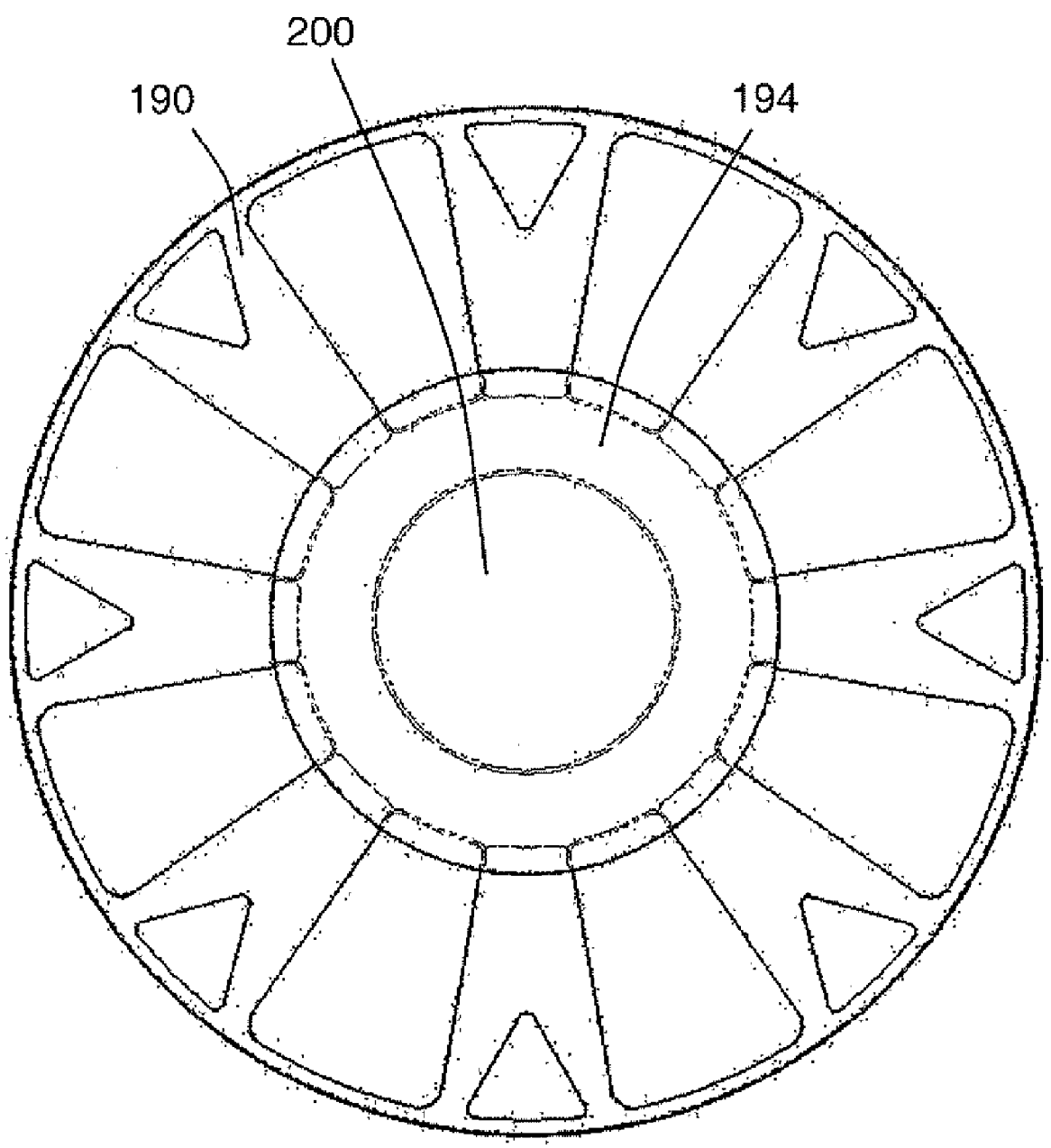
FIG. 21 is the plan drawing of the haptic and optic of FIG. 20, with additional hidden lines.

FIGS. 19 through 21 show another exemplary haptic 190 in various plan views, both with and without an optic 200. FIG. 19 is a plan drawing of a haptic 190. FIG. 20 is a plan drawing of the haptic 190 of FIG. 19, with an optic 200. FIG. 21 is the plan drawing of the haptic 190 and optic 200 of FIG. 20, with additional hidden lines.

The haptic 190 of FIGS. 19 through 21 has eight filaments denoted by elements 191a through 191h. Alternatively, the haptic 190 may have more or fewer than eight filaments. Filaments 191a-h may have non-uniformities along their lengths, such as width variations, height variations, and/or holes 192a-h.

The holes 192a-h may desirably alter the mechanical properties of the respective filaments, so that a given zonular force may be transmitted efficiently into a distortion of the optic. The holes 192a-h may be triangular in shape, or may be any other suitable shape, such as round, square, rectangular, polygonal, and may optionally have one or more rounded corners and/or edges. Each hole may optionally vary in profile along its depth. There may optionally be more than one hole per filament. There may optionally be differing numbers of holes for different filaments. There may optionally be differently-shaped holes on the same filament.

Unlike the filaments 121a-h of FIGS. 12 through 18, the filaments 191a-h are connected at both their outermost edge and their innermost edge. The filaments 191a-h are joined at an outer annular ring 193 and an inner annular ring 194. The inner annular ring 194 may lie within the circumference of the optic 200, as in FIGS. 19 through 21. Alternatively, the inner annular ring 194 may lie outside the circumference of the optic 200, or may straddle the circumference of the optic 200.

The dimensions of the inner annular ring 194, specifically, the inner and outer diameters of the inner annular ring 194, may be determined in part by the stiffness of the haptic 190 and/or the stiffness of the optic 200. For instance, a stiffer haptic may require relatively little material, and the ratio may be fairly close to 1. Alternatively, a less stiff haptic may require more material, and the ratio may deviate significantly from 1.

Figure 22:
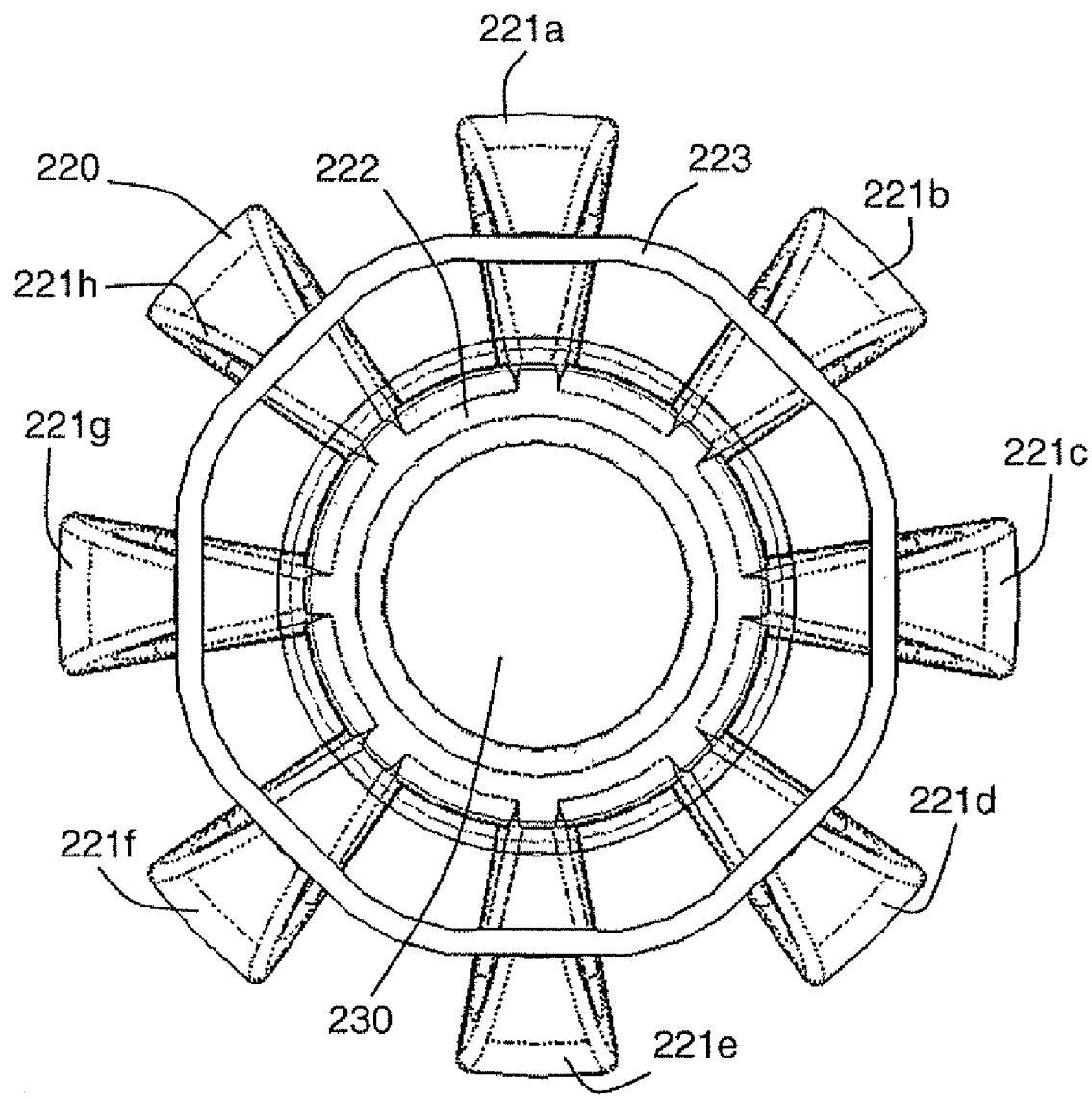
FIG. 22 is a top-view plan drawing of a haptic with an optic.
Figure 23:
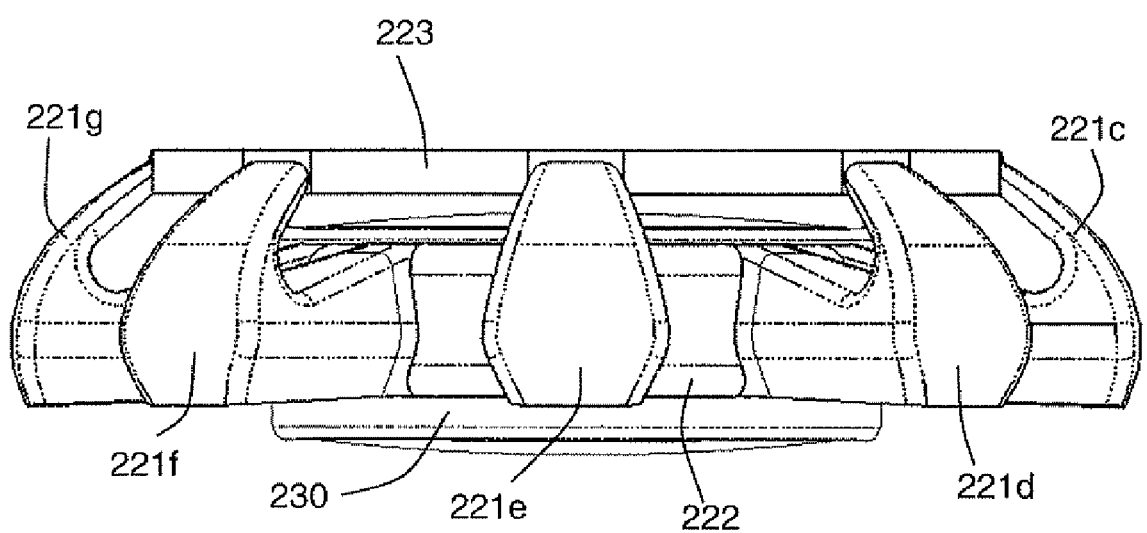
FIG. 23 is a side-view plan drawing of the haptic and optic of FIG. 22.
Figure 24:
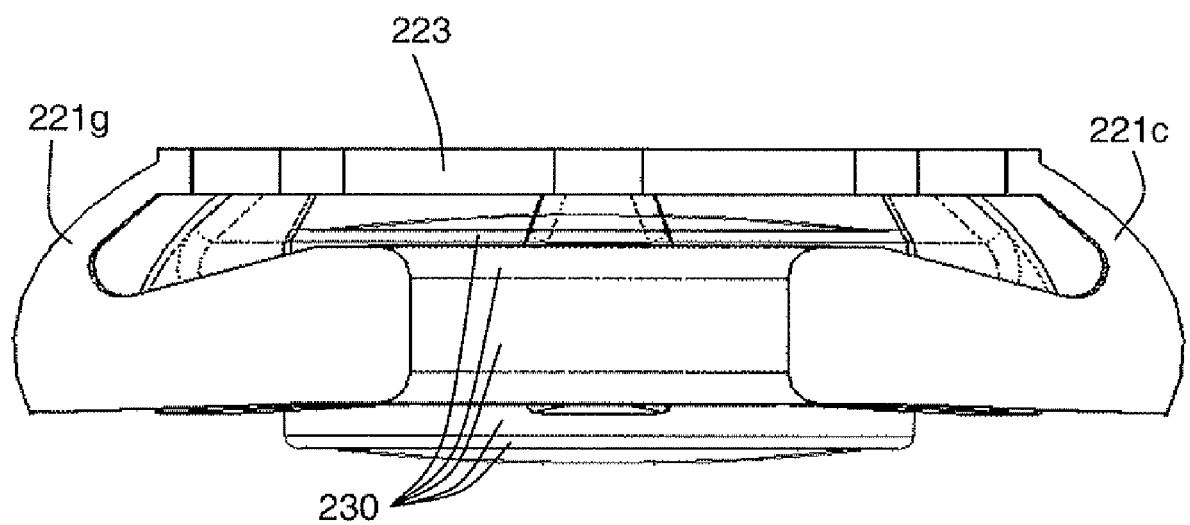
FIG. 24 is a side-view cross-sectional drawing of the haptic and optic of FIG. 22.
Figure 25:
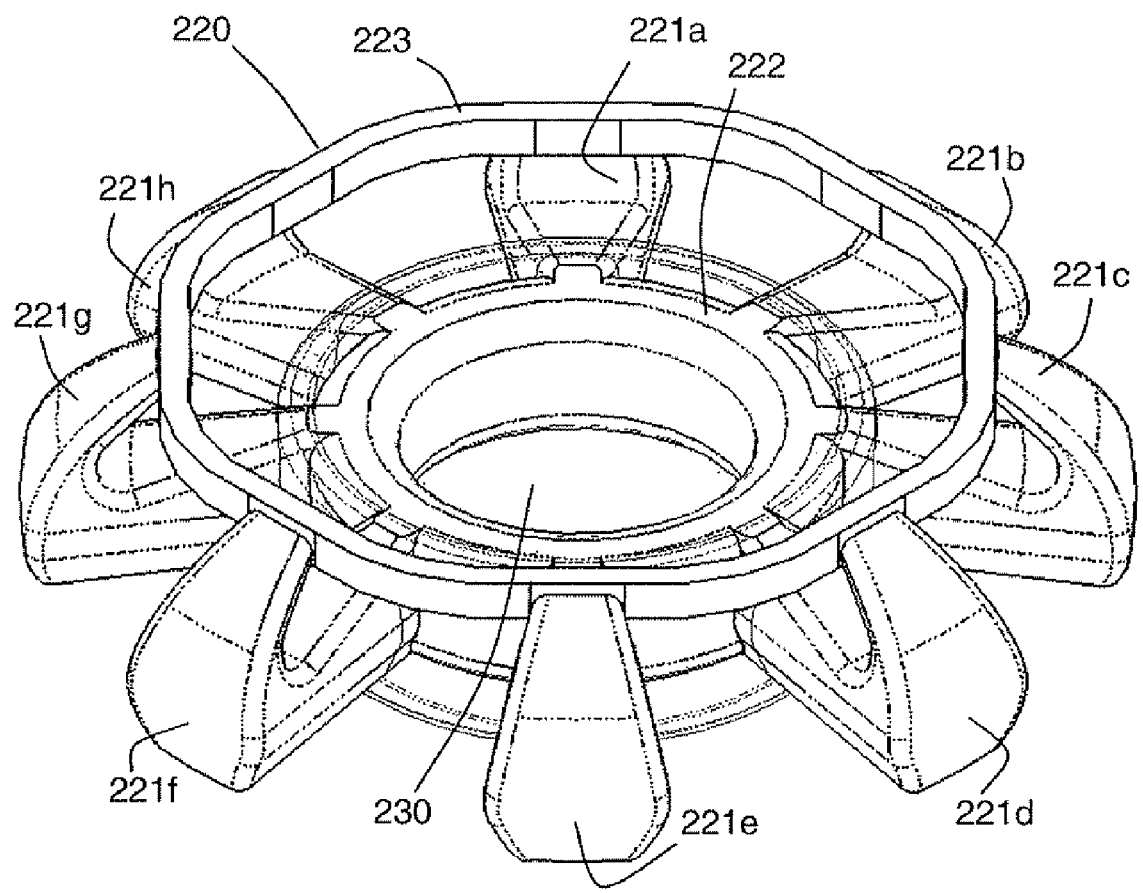
FIG. 25 is a plan drawing of the haptic and optic of FIG. 22.
Figure 26:
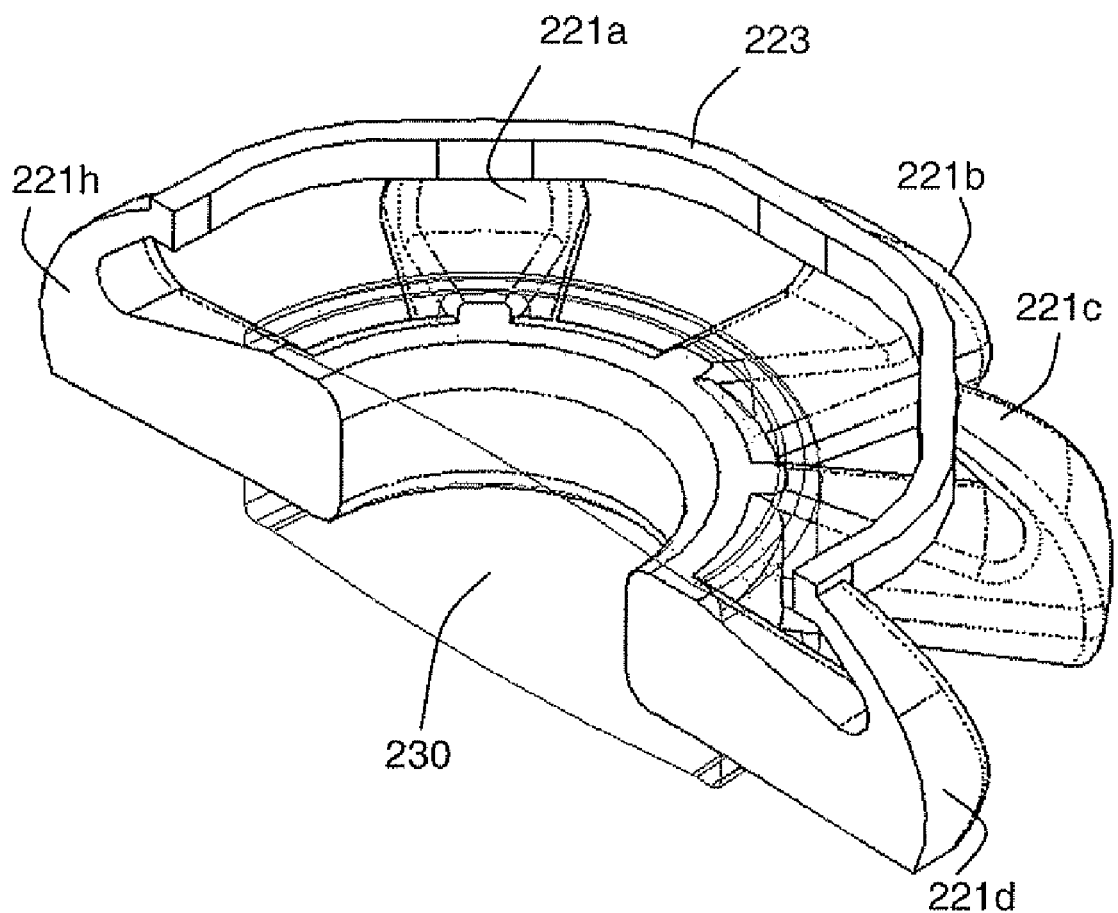
FIG. 26 is a cross-sectional drawing of the haptic and optic of FIG. 22.

FIGS. 22 through 26 show another exemplary haptic 220 in various plan views, with an optic 230. FIG. 22 is a top-view plan drawing of a haptic 220 with an optic 230. FIG. 23 is a side-view plan drawing of the haptic 220 and optic 230 of FIG. 22. FIG. 24 is a side-view cross-sectional drawing of the haptic 220 and optic 230 of FIG. 22. FIG. 25 is a plan drawing of the haptic 220 and optic 230 of FIG. 22. FIG. 26 is a cross-sectional drawing of the haptic 220 and optic 230 of FIG. 22.

The haptic 220 of FIGS. 22 through 26 has a more complex shape than the haptics shown in FIGS. 12 through 21. The haptic 220 has eight filaments 221a-h, each of which has one end attached to an inner annular ring 222 and has the opposite end attached to an outer annular ring 223. Alternatively, the haptic 220 may have more or fewer than eight filaments. In contrast with the haptics of FIGS. 12 through 21, the haptic 220 contacts the capsular bag of the eye at one or more points along the filaments 221a-h between the inner and outer annular rings 222 and 223. In some embodiments, the filaments 221a-h may loop back on themselves, and may contact the capsular bag at one or more extrema along the loop, rather than at the outer annular ring 223.

As with the inner annular ring 194 of FIGS. 19 through 21, the inner annular ring 222 may lie inside the circumference of the optic 230, once the optic 230 is placed within the haptic 220, may lie outside the circumference of the optic 230, or may straddle the circumference of the optic 230.

In some embodiments, such as the disc-shaped intraocular lenses shown in FIGS. 12 through 21, the haptic filaments engage an equatorial region of the capsular bag. In many of these embodiments, the optical power of intraocular lens may be selected to provide a disaccommodative bias, although some embodiments may alternatively provide an accommodative bias.

In other embodiments, the haptic filaments may engage substantially the entire capsular bag, rather than just the equatorial region of the capsular bag. In some of these embodiments, the filaments may extend generally in a plane that includes the optical axis of the lens, and there may be uncontacted portions of the capsular bag in the regions between the filaments. In many of these embodiments, the intraocular lens has an accommodative bias, although some embodiments may alternatively use a disaccommodative bias.

For the designs of FIGS. 12 through 26, the haptic may be pre-stressed, and the optic nay then be molded onto or attached to the haptic while the haptic is in the pre-stressed state. For instance, the haptic may be compressed or expanded radially prior to placing the optic within the haptic. The pre-stress may then be removed, and the lens may be allowed to relax to its substantially unstressed state, or a "natural" state. For a haptic that is much stiffer than the optic, the haptic may expand/contract by nearly the full compression/expansion amount, and the optic becomes expanded/compressed about its equator. In its expanded state, the optic is under radial tension.

This pre-stress may help reduce or eliminate buckling of the optic, if the optic is compressed. It may also reduce the need for a thicker optic for maximizing the power change for a given external force (e.g., an ocular force produced by the ciliary muscle, the zonules, and/or the capsular bag of the eye.) Furthermore, the pre-stress may allow for a so-called "fail-safe" design that allows only a certain amount of power change during accommodation; the lens may minimize the power change beyond a prescribed accommodation range. In addition, the pres-stress may reduce the amount of force required for a given power change.

The description of the invention and its applications as set forth herein is illustrative and is not intended to limit the scope of the invention. Variations and modifications of the embodiments disclosed herein are possible, and practical alternatives to and equivalents of the various elements of the embodiments would be understood to those of ordinary skill in the art upon study of this patent document. These and other variations and modifications of the embodiments disclosed herein may be made without departing from the scope and spirit of the invention.

What is claimed is:

1. An intraocular lens for implantation in a capsular bag of an eye, comprising:
    an adjustable optic disposed about an optical axis having an axial thickness through the center thereof, an anterior face, and a posterior face, the faces configured to provide a lens power; and
    a haptic including a portion protruding into the adjustable optic, the haptic portion having a maximum axial thickness that is at least one half the axial thickness of the adjustable optic;
    wherein the haptic is configured to transmit forces to alter at least one of the shape and the thickness of the adjustable optic;
    wherein the protruding portion is disposed between the anterior and posterior faces of the optic in a direction along the optical axis;
    wherein the haptic has essentially the same refractive index as the adjustable optic.

2. The intraocular lens of claim 1, wherein the haptic protrudes into the edge of the adjustable optic.

3. The intraocular lens of claim 1, wherein the adjustable optic has a stiffness less than 500 kPa.

4. The intraocular lens of claim 3, wherein the adjustable optic has a stiffness between 0.5 kPa and 500 kPa.

5. The intraocular lens of claim 4, wherein the adjustable optic has a stiffness between 25 kPa and 200 kPa.

6. The intraocular lens of claim 5, wherein the adjustable optic has a stiffness between 25 kPa and 50 kPa.

7. The intraocular lens of claim 1, wherein the haptic comprises at least two materials having different stiffnesses.

8. The intraocular lens of claim 1, wherein the force is a radial ocular force.

9. The intraocular lens of claim 1, wherein the entire protruding portion is disposed between the adjustable optic in a direction along the optical axis.

10. The intraocular lens of claim 1, wherein the adjustable optic includes an anterior face and a posterior face, the faces being circular when viewed from a direction along the optical axis.

11. The intraocular lens of claim 1, wherein a dispersion function for the haptic and a dispersion function for the optic have the same value at one wavelength of light between 400 nm and 700 nm.

12. The intraocular lens of claim 1, wherein a dispersion function for the haptic and a dispersion function for the optic have the same value at more than one wavelength of light between 400 nm and 700 nm.

13. The intraocular lens of claim 1, wherein the haptic includes a portion protruding into the adjustable optic extending from a region around a circumference of the adjustable optic and into a clear aperture of the adjustable optic.

14. An intraocular lens for implantation in a capsular bag of an eye, comprising:
    an adjustable optic disposed about an optical axis having an axial thickness through the center thereof, an anterior face, and a posterior face, the faces configured to provide a lens power; and
    a haptic including a portion protruding into the adjustable optic, the haptic portion having a maximum axial thickness that is at least one half the axial thickness of the adjustable optic;

wherein the haptic is configured to transmit forces to alter at least one of the shape and the thickness of the adjustable optic;

wherein the protruding portion is disposed between the anterior and posterior faces of the optic in a direction along the optical axis;

wherein the haptic includes a plurality of radial segments that are shaped to engage an equatorial region of the capsular bag.

15. A method of adjusting the focus of an intraocular lens having an adjustable optic having an annular recess, comprising:

applying a deforming force through a haptic in contact with the adjustable optic; and altering at least one parameter of the adjustable optic in response to the deforming force;

applying the deforming force to create an asymmetric deformation of the adjustable optic;

wherein:

the adjustable optic is disposed about an optical axis having an axial thickness through the center thereof;

the haptic includes a portion protruding into the adjustable optic;

the haptic portion has a maximum axial thickness that is at least one half the axial thickness of the adjustable optic; and the protruding portion is disposed between the anterior and posterior faces of the optic in a direction along the optical axis.

16. The method of claim 15, wherein the at least one parameter comprises an anterior radius of curvature of the adjustable optic.

17. The method of claim 15, wherein the at least one parameter comprises a posterior radius of curvature of the adjustable optic.

18. The method of claim 15, wherein the at least one parameter comprises a thickness of the adjustable optic.

19. An intraocular lens for implantation in a capsular bag of an eye, comprising:

an adjustable optic disposed about an optical axis having an axial thickness through the center thereof, an anterior face, and a posterior face, the faces configured to provide a lens power; and a haptic including a portion protruding into the adjustable optic, the haptic portion having a maximum axial thickness that is at least one half the axial thickness of the adjustable optic;

wherein the haptic is configured to transmit forces to alter at least one of the shape and the thickness of the adjustable optic;

wherein the protruding portion is disposed between the anterior and posterior faces of the optic in a direction along the optical axis;

further comprising a plurality of haptics each including a portion protruding into the adjustable optic, the haptic portions having a maximum axial thickness that is at least one half the axial thickness of the adjustable optic;

wherein the total number of haptics is greater than two.

20. The intraocular lens of claim 19, wherein each haptic has a proximal portion protruding into the adjustable optic and a distal portion outside the adjustable optic, the proximal portions being joined together by a ring structure.

21. The intraocular lens of claim 19, wherein each haptic has a proximal portion protruding into the adjustable optic and a distal portion outside the adjustable optic, the distal portions being joined together by a ring structure.

22. The intraocular lens of claim 19, wherein each haptic has a proximal portion protruding into the adjustable optic and a distal portion outside the adjustable optic, both the proximal portion being joined together by a ring structure and the distal portion being joined together by a ring structure.

23. An intraocular lens for implantation in a capsular bag of an eye, comprising:

an adjustable optic disposed about an optical axis having an axial thickness through the center thereof, an anterior face, and a posterior face, the faces configured to provide a lens power; and a haptic including a portion protruding into the adjustable optic, the haptic portion having a maximum axial thickness that is at least one half the axial thickness of the adjustable optic;

wherein the haptic is configured to transmit forces to alter at least one of the shape and the thickness of the adjustable optic;

wherein the protruding portion is disposed between the anterior and posterior faces of the optic in a direction along the optical axis;

wherein a plane containing the optical axis defines a cross-sectional curve profile at the intersection of the adjustable optic and the haptic, the curve containing endpoints at a periphery of the adjustable optic;

wherein the cross-sectional curve profile has a maximum thickness in a direction along the optical axis that is at least one half a maximum axial thickness of the adjustable optic.

24. An intraocular lens for implantation in a capsular bag of an eye, comprising:

an adjustable optic disposed about an optical axis having an axial thickness through the center thereof, an anterior face, and a posterior face, the faces configured to provide a lens power; and a haptic including a portion protruding into the adjustable optic, the haptic portion having a maximum axial thickness that is at least one half the axial thickness of the adjustable optic;

wherein the haptic is configured to transmit forces to alter at least one of the shape and the thickness of the adjustable optic;

wherein the protruding portion is disposed between the anterior and posterior faces of the optic in a direction along the optical axis;

wherein a plane containing the optical axis defines a cross-sectional curve profile at the intersection of the adjustable optic and the haptic, the curve containing endpoints at a periphery of the adjustable optic;

wherein the cross-sectional curve profile has constant thickness in a direction along the optical axis over a predetermined length perpendicular to the optical axis.

25. An intraocular lens for implantation in a capsular bag of an eye, comprising:

an adjustable optic disposed about an optical axis having an axial thickness through the center thereof, an anterior face, and a posterior face, the faces configured to provide a lens power; and haptic including a portion protruding into the adjustable optic, the haptic portion having a maximum axial thickness that is at least one half the axial thickness of the adjustable optic;

wherein the haptic is configured to transmit forces to alter at least one of the shape and the thickness of the adjustable optic;

wherein the protruding portion is disposed between the anterior and posterior faces of the optic in a direction along the optical axis;

wherein a plane containing the optical axis defines a cross-sectional curve profile at the intersection of the adjustable optic and the haptic, the curve containing endpoints at a periphery of the adjustable optic;

wherein at least a portion of the cross-sectional curve profile has thickness in a direction along the optical axis that decreases with radial distances from the optical axis.

26. An intraocular lens for implantation in a capsular bag of an eye, comprising:

an adjustable optic disposed about an optical axis having an axial thickness through the center thereof, an anterior face, and a posterior face, the faces configured to provide a lens power; and a haptic including a portion protruding into the adjustable optic, the haptic portion having a maximum axial thickness that is at least one half the axial thickness of the adjustable optic;

wherein the haptic is configured to transmit forces to alter at least one of the shape and the thickness of the adjustable optic;

wherein the protruding portion is disposed between the anterior and posterior faces of the optic in a direction along the optical axis;

wherein the haptic portion has a maximum axial thickness that is at least 75% of a maximum axial thickness of the adjustable optic along the optical axis.

* * * * *

UNITED STATES PATENT AND TRADEMARK OFFICE
Certificate

Patent 7,713,299 B2                                                    Patented: May 11, 2010

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Daniel G. Brady, San Juan Capistrano, CA (US); Tuyet Hoc Nguyen, Orange, CA (US); Henk A. Weeber, Groningen (NL); Douglas S. Cali, Mission Viejo, CA (US); Timothy R. Bumbalough, Fullerton, CA (US); and Edward P. Geraghty, Rancho Santa Margarita, CA (US).

Signed and Sealed this Twenty-eighth Day of June 2011.

<div style="text-align:right">

CORRINE M. MCDERMOTT
*Supervisory Patent Examiner*
Art Unit 3738
Technology Center 3700

</div>